US010460829B2

(12) United States Patent
Murray

(10) Patent No.: US 10,460,829 B2
(45) Date of Patent: Oct. 29, 2019

(54) SYSTEMS AND METHODS FOR ENCODING GENETIC VARIATION FOR A POPULATION

(71) Applicant: Seven Bridges Genomics Inc., Cambridge, MA (US)

(72) Inventor: Benjamin Murray, London (GB)

(73) Assignee: SEVEN BRIDGES GENOMICS INC., Cambridge, MA (US)

( * ) Notice: Subject to any disclaimer, the term of this patent is extended or adjusted under 35 U.S.C. 154(b) by 731 days.

(21) Appl. No.: 15/006,391

(22) Filed: Jan. 26, 2016

(65) Prior Publication Data

US 2017/0211205 A1 Jul. 27, 2017

(51) Int. Cl.
| | | |
|---|---|---|
| G16B 35/00 | (2019.01) | |
| H03M 7/30 | (2006.01) | |
| G16H 10/60 | (2018.01) | |
| G16B 20/00 | (2019.01) | |
| G16C 20/60 | (2019.01) | |

(52) U.S. Cl.
CPC ............ *G16B 35/00* (2019.02); *G16B 20/00* (2019.02); *G16C 20/60* (2019.02); *G16H 10/60* (2018.01); *H03M 7/60* (2013.01)

(58) Field of Classification Search
CPC ........... H03M 7/48; H03M 7/46; G06F 19/18; G16Z 99/00
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,321,623 B2 | 1/2008 | Dambrackas |
| 7,483,585 B2 | 1/2009 | Brakus, Jr. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,972,201 B2 | 3/2015 | Mande et al. |
| 9,063,914 B2 | 6/2015 | Kural et al. |
| 9,092,402 B2 | 7/2015 | Kural et al. |
| 9,116,866 B2 | 8/2015 | Kural |
| 2002/0164629 A1 | 11/2002 | Quake et al. |
| 2002/0190663 A1 | 12/2002 | Rasmussen |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0114362 A1 | 5/2007 | Feng et al. |
| 2007/0166707 A1 | 7/2007 | Schadt et al. |
| 2008/0003571 A1 | 1/2008 | McKernan et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |

(Continued)

FOREIGN PATENT DOCUMENTS

| | | |
|---|---|---|
| KR | 101282798 B1 | 7/2013 |
| WO | 2007/086935 A2 | 8/2007 |

(Continued)

OTHER PUBLICATIONS

Layer et al. Efficient compression and analysis of large genetic variation datasets. https://www.biorxiv.org/content/biorxiv/early/2015/04/20/018259.full.pdf, printed as pp. 1/19-19/19, available online Apr. 20, 2015. (Year: 2015).*

(Continued)

*Primary Examiner* — Jennifer Dunston
(74) *Attorney, Agent, or Firm* — Morgan, Lewis & Bockius LLP

(57) ABSTRACT

In one embodiment, a method of encoding variation data for a population comprises receiving, by a variant encoding engine executing on a processor, information describing genetic variation of a population of individuals. The information comprises a plurality of variable sites within the reference genome of the population and the genotypes of a plurality of individuals in the population with respect to those variable sites. The method further comprises selecting an encoding strategy for the information based on the characteristics of the genetic variation across the population, and encoding the information according to the selected encoding strategy. In certain embodiments, selecting an encoding strategy may comprise determining the variability of a variable site within the population, and encoding information associated with the variable site based on the variability.

11 Claims, 8 Drawing Sheets

(56) References Cited

U.S. PATENT DOCUMENTS

| | | |
|---|---|---|
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0137143 A1 | 6/2010 | Rothberg et al. |
| 2010/0169026 A1 | 7/2010 | Sorenson et al. |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0232480 A1 | 9/2013 | Winterfeldt et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0051588 A9 | 2/2014 | Drmanac et al. |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0112602 A1 | 4/2015 | Kural et al. |
| 2015/0112658 A1 | 4/2015 | Kural et al. |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015027050 A1 | 2/2015 |
| WO | 2015058093 A1 | 4/2015 |
| WO | 2015058095 A1 | 4/2015 |

OTHER PUBLICATIONS

Chanda et al. HapZipper: sharing HapMap populations just got easier. Nucleic Acids Research, vol. 40, No. 20, e159, Jul. 27, 2012 , printed as pp. 1/7-7/7. (Year: 2012).*

The International HapMap Consortium. A second generation human haplotype map of over 3.1 million SNPs. Nature, vol. 449, pp. 851-861, Oct. 2007, including 1 page of Methods. (Year: 2007).*
The International HapMap Consortium. A haplotype map of the human genome. Nature, vol. 437, pp. 1299-1320, Oct. 2005. (Year: 2005).*
The 1000 Genomes Project, 2015, A global reference for human genetic variation, Nature 526:68-74.
Li, 2010, A survey of sequence alignment algorithms for next-generation sequencing, Briefings in Bionformatics 11(5):473-483.
Durbin, 2014, Efficient haplotype matching and storage using the positional Burrows-Wheeler transform (PBWT), Bioinformatics 30(9):1266-1272.
Layer, 2015, Efficient genotype compression and analysis of large genetic-variation data sets, Nat Meth 13(1):63-65.
Layer, 2015, Efficient compression and analysis of large genetic variation datasets, Biorxiv preprint, available at http://biorxiv.org/content/early/2015/04/20/018259.
Li, 2015, BGT: efficient and flexible genotype query across many samples, arXiv:1506.08452 [q-bio.GN].
Li, 2015, Towards Better Understanding of Artificats in Variant Calling from High-Coverage Samples, arXiv:1404.0929 [q-bio.GN].
Popitsch, 2013, NGC: lossless and lossy compression of aligned high-throughput sequencing data, Nucl Acids Res, 41(1):e27.
Sudmant, 2015, An integrated map of structural variation in 2,504 human genomes, Nature 526:75-81.
Tewhey, 2011, The importance of phase information for human genomics, Nat Rev Gen 12:215-223.
The Variant Call Format (VCF) Version 4.2 Specification (Jan. 26, 2015), available at https://samtools.github.io/hts-specs/VCFv4.2.pdf.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioinformatics 29(10):1250-1259.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.

(56) References Cited

OTHER PUBLICATIONS

Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):556-564.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1:e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12):e1000589.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12 (1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, MOSAIK: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.

(56) References Cited

OTHER PUBLICATIONS

Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Wu, 2010, Fast and SNP-tolerant detection of complex variants and splicing in short reads, Bioinformatics, 26(7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Tavema plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break—Understanding and Combating Decay in Taverna Workflows, eScience 2012, Chicago, Oct. 2012.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Posada, 1998, Model Test: testing the model of DNA substitution, Bioinformatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.

(56) References Cited

OTHER PUBLICATIONS

Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing.pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinfomiatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).

(56) References Cited

OTHER PUBLICATIONS

International Search Report and Written Opinion dated Feb. 4, 2015, for Patent Application No. PCT/US2014/061158, filed Oct. 17, 2014, (11 pages).

International Search Report and Written Opinion dated Jan. 27, 2015, for International Patent Application No. PCT/US2014/060680, filed Oct. 215, 2014, (11 pages).

International Search Report and Written Opinion dated Sep. 2, 2016, for International Patent Application No. PCT/US2016/033201 with International Filing Date May 19, 2016 (14 pages).

International Search Report and Written Opinion dated Sep. 7, 2016, for International Application No. PCT/US2016/036873 with International Filing Date Jun. 10, 2016 (8 pages).

International Search Report and Written Opinion of the International Searching Authority dated Nov. 17, 2015 for International Application No. PCT/US2015/048891 (11 Pages).

Kano, 2010, Text mining meets workflow: linking U-Compare with Taverna, Bioinformatics 26(19):2486-7.

Katoh, 2005, MAFFT version 5: improvement in accuracy of multiple sequence alignment, Nucl Acids Res 33(2):511-518.

Kawas, 2006, BioMoby extensions to the Taverna workflow management and enactment software, BMC Bioinformatics 7:523.

Kehr, 2014, Genome alignment with graph data structures: a comparison, BMC Bioinformatics 15:99.

Kent, 2002, BLAT—The Blast-Like Alignment Tool, Genome Research 4:656-664.

Kim, 2005, ECgene: Genome-based EST clustering and gene modeling for alternative splicing, Genome Res 15:566-576.

Kim, 2008, A Scaffold Analysis Tool Using Mate-Pair Information in Genome Sequencing, Journal of Biomedicine and Biotechnology 8(3):195-197.

Kim, 2013, TopHat2: accurate alignment of transcriptomes in the presence of insertions, deletions and gene fusions, Genome Biol 14(4):R36.

Krabbenhoft, 2008, Integrating ARC grid middleware with Taverna workflows, Bioinformatics 24(9):1221-2.

Kuhn, 2010, CDK-Taverna: an open workflow environment for cheminformatics, BMC Bioinformatics 11:159.

Kumar, 2010, Comparing de novo assemblers for 454 transcriptome data, BMC Genomics 11:571.

\* cited by examiner

SYSTEMS AND METHODS FOR ENCODING GENETIC VARIATION FOR A POPULATION

FIELD OF THE DISCLOSURE

The present disclosure generally relates to systems and methods for representing information related to genetic variation within populations. In particular, the present disclosure relates to systems and methods for efficiently encoding and decoding variant information by leveraging characteristics of genetic variation in the context of population-sized data sets.

BACKGROUND

The number of fully sequenced genomes continues to grow, and with it our understanding of human genetic variation. For example, the 1000 Genomes Project is an international collaboration that seeks to provide a comprehensive description of common human genetic variation by performing whole-genome sequencing of a diverse set of individuals from multiple populations. To that end, the 1000 Genomes Project has sequenced the genomes of over 2,500 unidentified people from about 25 populations around the world. See "A global reference for human genetic variation", *Nature* 526, 68-74 (2015). This has led to new insights regarding the history and demography of ancestral populations, the sharing of genetic variants among populations, and the role of genetic variation in disease. Further, the sheer number of genomes has greatly increased the resolution of genome wide association studies, which seek to link various genetic traits and diseases with specific genetic variants.

The current standard format for storing and representing human genetic variation information is Variant Call Format (VCF). VCF is a text file format which stores information about genetic variation as a list of variations from a reference, such as the human genome. A VCF file contains meta-information lines, a header line, and then a plurality of data lines, each data line containing information about a particular position exhibiting variation in the reference sequence. For example, a data line can include the nucleotide sequence at that position and a list of alternative known alleles. The data line can further include information regarding the genotypes of a plurality of individuals at that position with respect to the reference sequence and alternative alleles. Genotypes are expressed as a pair of haplotypes: "0/0" indicates that the individual is homozygous for the reference sequence at that position; "0/1" indicates that the individual is heterozygous and has one chromosome with the alternative allele; and "1/1" indicates that the individual is homozygous for the alternative allele.

VCF is an expressive format that can accommodate multiple samples and is widely used in the community. However, as a text-based format, VCF files are large and slow to parse, especially as the number of genomes in a VCF file increases. File size can be reduced via compression, but this introduces an additional overhead component that makes working with VCF files further resource intensive. A more efficient format is BCF, which encodes VCF fields into a binary format that both reduces the amount of space required and also speeds up access times. For example, BCF can encode a genotype for an individual using only two bytes of information (e.g., "0/1" as "0x02 0x04"). BCF files can be compressed (e.g., by BGZF compression) to reduce their size further; however, like with VCF, compression introduces an overhead component that can slow query speeds. More often, it is convenient and practical to process and stream BCF files uncompressed.

BCF seeks to maximize the efficiency of storing and accessing variant information. However, the storage space required for the format scales linearly with the number of included individuals. Using two bytes per genotype, a single person requires 154 megabytes of storage. One hundred people require 15 gigabytes, and one thousand require 150 gigabytes. As the 1000 Genomes Project has shown, increasing the number of genomes by orders of magnitude greatly improves the power of analysis. Using uncompressed BCF at two bytes per genotype without any additional metadata, ten thousand people would require 1.47 terabytes, one million people would require 147 terabytes, and ten million people would require 1.44 petabytes. At this scale, computing resources can become too costly, and simply querying the data set can take an extraordinary amount of time, impacting meaningful analysis. Accordingly, there is a need for improvements in storing variant information for population sized data sets which does not suffer from the limitations described for the above approaches.

SUMMARY

The present disclosure features novel approaches for storing and representing information related to genetic variation within a population. The storage of population variant data is one of the largest upcoming challenges in genomics as the number of individuals in population data sets increases from thousands, to millions, and beyond. As a population data set increases, the number of variants expressed typically does not drastically change. However, due to falling costs in whole genome sequencing and the applicability of large data sets to genomic analyses, the number of people or individuals represented in a data set will likely change by orders of magnitude. Systems and methods according to the disclosure represent and access variant data in ways that scale well as the number of individuals in the population increases. In particular, systems and methods according to the disclosure efficiently encode variant data in a way that allows it to be accessible at large scales, enabling meaningful analysis of large variant populations.

The present disclosure results, in one example, from the realization that variant information for a population can be efficiently stored and encoded by leveraging properties that emerge when variant data is considered in the context of large populations. For example, the vast majority of variants in a population are very rare. These variants can be efficiently stored using a compression encoding scheme, such as a run length encoding scheme. However, the low percentage of variants that are relatively common across the population can be better stored using other means, such as by encoding each variant as a minimal number of bits. Further improvements in efficiency can be made by exploiting coherence across variants due to the presence of statistical associations between variations and defined haplotypes within the population. In particular, this presents a substantial improvement over conventional formats, which often lose the ability to use this information once it is encoded. These improvements allow for the ability to search and query variant information for populations comprising millions of people using only commodity hardware.

In one embodiment, a method of encoding variation data for a population comprises receiving, by a variant encoding engine executing on a processor, information describing genetic variation of a population of individuals. The information comprises a plurality of variable sites within the reference genome of the population and the genotypes of a plurality of individuals in the population with respect to those variable sites. An encoding strategy for the information is then selected based on the characteristics of the genetic variation across the population. Finally, the information is encoded according to the selected encoding strategy. In certain embodiments, the encoding strategy comprises a first encoding strategy and a second encoding strategy. In further embodiments, the first encoding strategy is different from the second encoding strategy.

In certain embodiments, the encoding strategy comprises encoding each genotype as a minimal number of bits. In certain embodiments, the encoding strategy comprises a compression encoding strategy. The compression encoding strategy can be a run length encoding strategy, for example. A run length encoding strategy can comprise, for each variable site of the plurality of variable sites, selecting the genotypes of the plurality of individuals for that variable site, wherein the genotypes comprise a sequence of symbols, the sequence of symbols comprising alternating runs of adjacent identical symbols. A run length is then determined for each run of adjacent identical symbols, and the sequence of symbols is then encoded as a plurality of symbols and run lengths. In certain embodiments, encoding each run length of the runs of adjacent identical symbols uses a variable bit format, wherein the variable bit format comprises a number of bits sufficient to encode the symbol and an associated run length. In further embodiments, the variable bit format comprises 1 bit to encode a symbol, and 3 bits to encode an associated run length.

In further embodiments, selecting the encoding strategy for the information based on the genetic variation comprises selecting a variable site in the population, determining the variability of the variable site in the population, and encoding the information associated with the variable sited based on its variability. For example, a highly variable site can be encoded using a first encoding strategy, and a low variable site can be encoded using a second encoding strategy. In certain embodiments, the first encoding strategy is a bit field encoding strategy, and the second encoding strategy is a run length encoding strategy. In certain embodiments, determining the variability of the variable site in the population can comprise calculating the number of run length entries required to encode the variable site. In further embodiments, the variable site can be encoded using a bit field encoding strategy if the size of the representation using a run length encoding strategy exceeds that of a bit field encoding strategy. In certain embodiments, the number of run length entries at which the bit field encoding strategy is used is about 313.

In certain embodiments, selecting an encoding strategy based on the characteristics of the genetic variation comprises identifying variable sites that occur together with statistical significance. Encoding the information according to the selected encoding strategy can comprise identifying a set of variable sites having alleles that occur together with a level of statistical significance. The actual combination of alleles for the identified set of variable sites may then be determined, and a unique value is assigned to each actual combination of alleles. The set of variable sites may then be encoded using the assigned unique values. In certain embodiments, identifying a set of variable sites having alleles that occur together with a level of statistical significance comprises identifying a set of variable sites having alleles that exhibit fewer combinations than would be expected by chance. In certain embodiments, the set of variable sites identified comprise those variable sites encoded using a bit field encoding strategy.

In another embodiment, a system for encoding variation data for a population comprises a memory and a processor. The memory stores information describing the genetic variation of a population of individuals, which comprises a plurality of variable sites within the reference genome of the population and the genotypes of a plurality of individuals in the population with respect to those variable sites. The processor executes instructions configured to, for each variable site in the population, determine the variability of the variable site in the population, and encode the information associated with the variable site based on the frequency of alternate alleles of the variable site occurring in the population. A variable site having a high frequency of alternate alleles is encoded using a bit field encoding strategy, and a variable site having a low frequency of alternate alleles is encoded using a run length encoding strategy.

BRIEF DESCRIPTION OF THE DRAWINGS

FIG. 1 is a block diagram illustrating an embodiment of a variant storage system according to the disclosure;

FIG. 2 is a block diagram illustrating another embodiment of a variant storage system according to the disclosure;

FIG. 3 is a block diagram illustrating the variant encoding engine and variant decoding engine of FIG. 1 in further detail;

FIG. 4 is a flow diagram illustrating an embodiment of a method of encoding variant information based on the prevalence of each variant in a population;

FIG. 5 is a chart depicting a relationship between prevalence and performance of an encoding strategy;

FIG. 6 is a flow diagram illustrating an embodiment of a method for encoding variants by defining haplotypes within a variant set;

FIG. 7 is a flow diagram illustrating an embodiment of a method for identifying haplotypes within a variant set; and FIG. 8 is a flow diagram illustrating another embodiment of a method for efficiently encoding variation data for a population.

DETAILED DESCRIPTION OF THE DISCLOSURE

Figure 1:
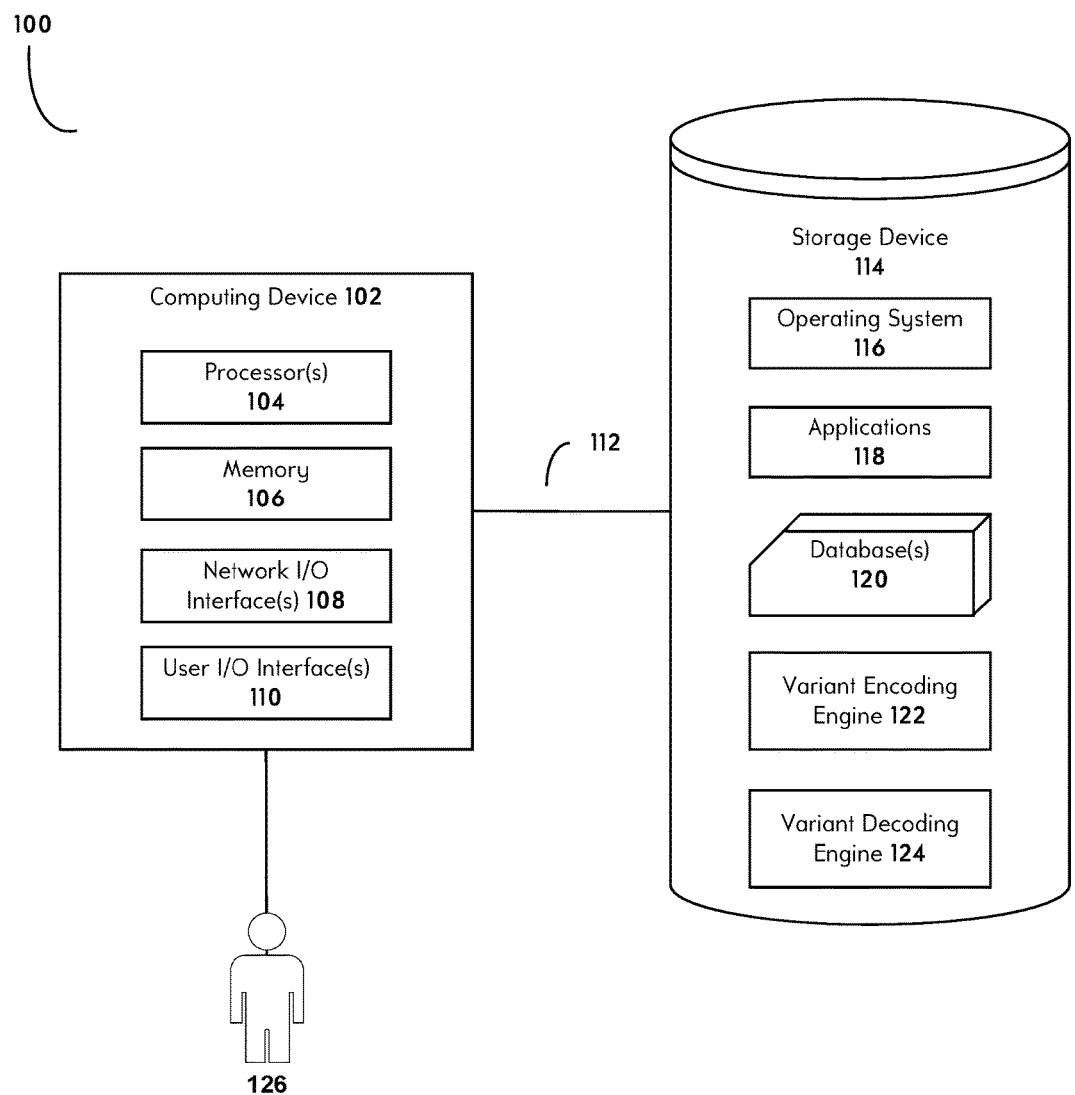
FIGS. 1 through 8, wherein like parts are designated by like reference numerals throughout, illustrate an example embodiment of a system and method for the implementation of a variant storage system. Although the present disclosure describes the system and method with reference to the example embodiments described in the figures, it should be understood that many alternative forms can embody the present disclosure. One of ordinary skill in the art will additionally appreciate different ways to alter the parameters of the embodiments disclosed in a manner still in keeping with the spirit and scope of the present disclosure.

Embodiments of the disclosure describe novel systems and methods for encoding and decoding variation data for a population that scales efficiently as the number of individuals in the population increases. In particular, systems and methods according to the disclosure solve problems unique to the fields of genomics and bioinformatics, problems that are growing given the exponential growth of modern technologies such as next-generation DNA sequencing. This can include multiple inventive steps, such as representing variants as a minimal number of bits; encoding variants using a compression encoding scheme, such as run length encoding;

choosing an encoding scheme based on characteristics of variants across the population, such as their prevalence; and leveraging other properties, such as statistical associations between variants, that are present in population-sized data sets. The practical result is a highly condensed and compressed store of variation data that requires little overhead for decoding and accessing. Accordingly, genetic variation data for entire populations can be encoded, stored, and queried using only commodity hardware, such as a laptop computer. Thus, systems and methods according to the invention improve the functioning of the computer itself, democratizing access to previously unavailable large variation data stores, and thus provide substantial benefits to scientific and medical research.

Further, the detailed description set forth below in connection with the appended drawings is intended as a description of embodiments and does not represent the only forms which may be constructed and/or utilized. However, it is to be understood that the same or equivalent functions and sequences may be accomplished by different embodiments that are also intended to be encompassed within the spirit and scope of the disclosure.

For purposes of the disclosure, the terms "variant", "variable site", or "variation" refer to a site or location within a genome that exhibits variability across a population. A variant may represent any kind of genomic variation, such as the presence of single nucleotide polymorphisms (SNPs), short insertions and deletions (indels), larger structural variants (SVs), and the like. Each variant may have two or more alleles. The first allele represents the unchanged sequence for the reference genome at a position. The second allele represents a variation from the reference genome at that position. Other observed variations at that position can be represented by additional alleles. Variants exhibiting only two alleles for a population can be referred to as bi-allelic, and three alleles can be referred to as tri-allelic. For diploid organisms (having two copies of each chromosome), each individual in the population will possess two copies of each variant. Further, a population may refer to a plurality of individuals or organisms having the same genome, and may refer to data sets of any size, such as those comprising 10, 100, 1000, 10,000, 100,000, 1,000,000, or more individuals.

Variant data can be generated in a variety of ways. In one embodiment, variant data can be generated for a plurality of individuals using next-generation sequencing. Next-generation sequencing refers to methods of performing DNA sequencing that typically generate short (50-200 bp) nucleotide sequences, or sequence reads, compared to traditional DNA sequencing methods such as Sanger sequencing. However, next-generation sequencing compensates for this deficit with quantity. For example, the HiSeq2500 system (commercially available from Illumina, Inc., San Diego, Calif.) can generate over 300 million individual sequence reads per run. Sequence reads may then subsequently be mapped to a reference genome (e.g., the Genome Reference Consortium Grch38 human genome) using sophisticated algorithms and software programs, such as Bowtie, BWA, Mosaik, and the like. More information regarding sequencing alignment for next-generation sequencing can be found in Li, H., Homer, N., "A survey of sequence alignment algorithms for next-generation sequencing," *Brief Bioinform.*, 2010 September; 11(5):473-83.

Once sequence reads are mapped, mismatches between the sequence reads and the reference may be determined (e.g., using software programs such as VCFtools, GATK Haplotyper, and the like) to identify positions within the subject's genome that differ from the reference genome. As previously noted, positions within the reference genome that exhibit variation across a population are considered variants. Once variants have been identified, each subject's genotype with respect to that variant may be stored for later access using the VCF/BCF formats, for example. Storing variants in this manner can be used to provide a comprehensive description of human genetic variation for a population, enabling powerful studies to understand the history and demography of ancestor populations, the sharing of genetic variants among populations, and to identify variants associated with cancer and genetic disease. However, as the number of individuals in a population data set increases, conventional formats for storing genotype data present a severe bottleneck in analysis. Accordingly, systems and methods according to the present disclosure solve these problems by uniquely leveraging characteristics of large, population-sized data sets to efficiently encode and decode variant data for storage and subsequent analysis, allowing for thousands to millions of variants to be queried and studied using only commodity hardware.

In particular, while the number of people in a variant data set may increase by several orders of magnitude (e.g., a dataset of 1 million people represents a 400× increase over the 1000 Genomes Project), the number of variants is not expected to change to the same extent. This is because most variants in a population are rare; new individuals introduced to a population sized data set are more likely to have genotypes relating to already present variants, as opposed to having multiple new variants. Thus, systems and methods according to the disclosure exploit this property to represent variant data in a manner that scales well as the number of individuals in the population increases.

I. Exemplary Variant Storage Systems

FIG. 1 is a block diagram illustrating an embodiment of a variant storage system 100 suitable for practicing exemplary embodiments of the present disclosure. The variant storage system 100 may be used for storing variation data for a population, encoding variation data for a population, determining characteristics of variants in a population, efficiently encoding variants, and quickly decoding variants, for example. In this embodiment, the variant storage system 100 comprises a computing device 102, which may include processor(s) 104, memory 106, network input/output (I/O) interfaces 108, and user I/O interfaces 110. The variant storage system 100 may further comprise a storage device 114, such as a hard drive, flash drive, CD-ROM, or DVD, for storing an operating system 116 and other software programs. These software programs can include applications 118, which may further comprise a variant encoding engine 122 and a variant decoding engine 124. The storage device 114 may also store information related to variants, individuals, populations, and other data or information associated with the variant storage system 100, some of which may be stored within database(s) 120. The storage device 114 may be connected to the computing device 102 by a communications link 112.

Depending on particular implementation requirements of the present disclosure, the computing device 102 may be any type of computing system, such as a workstation, server, desktop computer, laptop, handheld computer, mobile device, tablet device, personal digital assistant, or any other form of computing device or system. The computing device 102 may have sufficient processing power and memory capacity to perform all or part of the operations described herein. Alternately, all or parts of the computing device 102 may serve as a proxy, with some or all functions performed externally by a computer or other computing device. The computing device 102 may be embodied as a stand-alone system, or as a component of a larger electronic system within any kind of environment, such as within a laboratory, data center, cloud computing environment, and the like. In certain embodiments, the variant storage system 100 may comprise multiples of computing devices 102, which may be differently configured.

The processors 104 may include hardware or software based logic to execute instructions on behalf of the computing device 102. For example, depending on specific implementation requirements, the processors 104 may include a microprocessor; single or multiple cores for executing software stored in the memory 106; or other hardware or software components for controlling the computing device 102. The processor 104 may be in communication with other components of the variant storage system 100, such as the memory 106, network I/O interfaces 108, user I/O interfaces 110, and storage device 114, for example, via a local bus.

The computing device 102 may access an external network or other computing devices via one or more network I/O interfaces 108. The network I/O interfaces 108 allows the computing device 102 to communicate with other computers or devices, and may comprise either hardware or software interfaces between equipment or protocol layers within a network. For example, the network I/O interfaces 108 may comprise Ethernet interfaces, frame relay interfaces, cable interfaces, DSL interfaces, token ring interfaces, wireless interfaces, cellular interfaces, serial interfaces fiber optic interfaces, and the like. Further, the computing device 102 may use the network I/O interfaces 108 to access various external data sources or services, provide access to data or information generated by the computing device 102 to various client devices, or receive instructions or allow access to functions using an Application Programming Interface (API), for example.

An end user 126 may interact with the computing device 102 and variant storage system 100 via one or more user I/O interfaces 110. The user I/O interfaces 110 may comprise any combination of input or output devices that allow an end user to interact with the computing device 102. For example, input devices may comprise a keyboard, touchscreen, microphone, camera, mouse, touchpad, trackball, and/or any combination thereof. Output devices may comprise a screen, speaker, printer, and/or any combination thereof. Thus, an end user may interact with the computing device 102 by speaking, tapping, gesturing, typing, or using a combination of multiple input modes. In turn, the computing device 102 or other component may respond with any combination of visual, aural, or haptic output. The computing device 102 may manage the user I/O interfaces 110 and provide a user interface to the end user by executing a stand-alone application (e.g., one of the applications 118) residing in the storage device 114 which has been loaded into the memory 106. Alternately, a user interface may be provided by an operating system 116 executing on the computing device 102.

The storage device 114 may be any form of storage, such as a hard disk, sold state drive, flash drive, DVD, CD-ROM, or cloud-based storage. The computing device 102 may access the storage device 114 via the communications link 112, which may comprise any form of electrical communication, including TCP/IP over a LAN or WAN network, or a direct connection such as USB or SATA. The communications link 112 may also simply be a local bus through which various components of the computing device 102 communicate. Accordingly, in certain embodiments, the computing device 102 and storage device 114 are housed within the same enclosure. However, in other embodiments, the computing device 102 and storage device 114 may be housed separately. In certain embodiments, several storage devices 114 may be used by the variant storage system 100. For example, various components of the storage device 114 may be distributed or duplicated between a local storage device residing on the computing device 102, and an external storage device accesses via a network or other communication means.

The applications 118, variant encoding engine 122, and variant decoding engine 124 may run on the operating system 116. The operating system 116 may comprise any of the versions of the conventional operating systems, any embedded operating system, any real-time operating system, any open source operating system, any proprietary operating system, or any other operating system capable of running on the computing device 102 and performing all or part of the operations described herein. Further, the operating system 116, applications 118, variant encoding engine 122, and variant decoding engine 124 may in some instances be accessed or run from a bootable CD, thumb drive, or from a network.

Applications 118 may comprise any kind of application, and may communicate and exchange data with other applications executing on the computing device 102. Applications may include applications related to various aspects of efficiently representing, storing, and accessing variant information for a population, for interacting with the computing device 102, for exchanging information with other components of the system, or for any other purpose. Applications 118 such as the variant encoding engine 122 and variant decoding engine 124 may execute entirely on the computing device 102, or alternately may execute at least partly on external computing devices or systems. For example, in certain embodiments, portions of the variant decoding engine 124 may execute on a separate computing device 102.

Information related to the variant storage system, such as variants, reference genomes, individuals, and the like may be stored within the database(s) 120. In certain embodiments, the database(s) 120 can comprise multiple databases, some of which may be stored externally and accessible over a network, for example. In certain embodiments, the database(s) 120 may comprise one or more relational databases comprising one or more relational or non-relational database tables. For example, the database(s) 120 can comprise one or more MySQL, MariaDB, SQLite, Microsoft SQL Server, PostgreSQL, MongoDB, and/or other NoSQL databases, and/or other relational or semantic databases. However, in certain embodiments, all or portions of the database(s) 120 may simply be a flat file.

The end user 126 may be any person, entity, or agent who interacts with the variant storage system 100 to access variant information. For example, the end user 126 may be a researcher wishing to access variant data for a population of cancer patients. However, the end user 126 also be any person or individual that interacts with the variant storage system 100 in some way. The end user 126 may interact directly with the computing device 102 via the user I/O interfaces 110 and/or the operating system 116 to encode, decode, or simply access variant information. The end user 126 may also interact with a specialized application in order to use various components of the variant storage system 100. Similarly, the end user 126 may also interact with the variant storage system 100 by way of an API available over the network I/O interfaces 108.

As previously noted, the storage device 114 may also store information related to variants, such as a position within a reference genome, the set of possible alleles, the encoding scheme used, and a position in memory. However, in certain embodiments, portions of the storage device 114 and variant storage system 100 may also store various other kinds of information and metadata related to variant data for populations. For example, the storage device 114 may include information and metadata regarding populations, such as the number of individuals in the population, their demographics, age, clinical history, and the like. Similarly, information and metadata may be stored that relates to individual variants or sets of variants, such as known disposition to disease, prevalence in the population, or interactions between variants. Information may be stored and organized in any manner or format, such as within a relational database, a semantic database, or as a simple flat-file.

Figure 2:
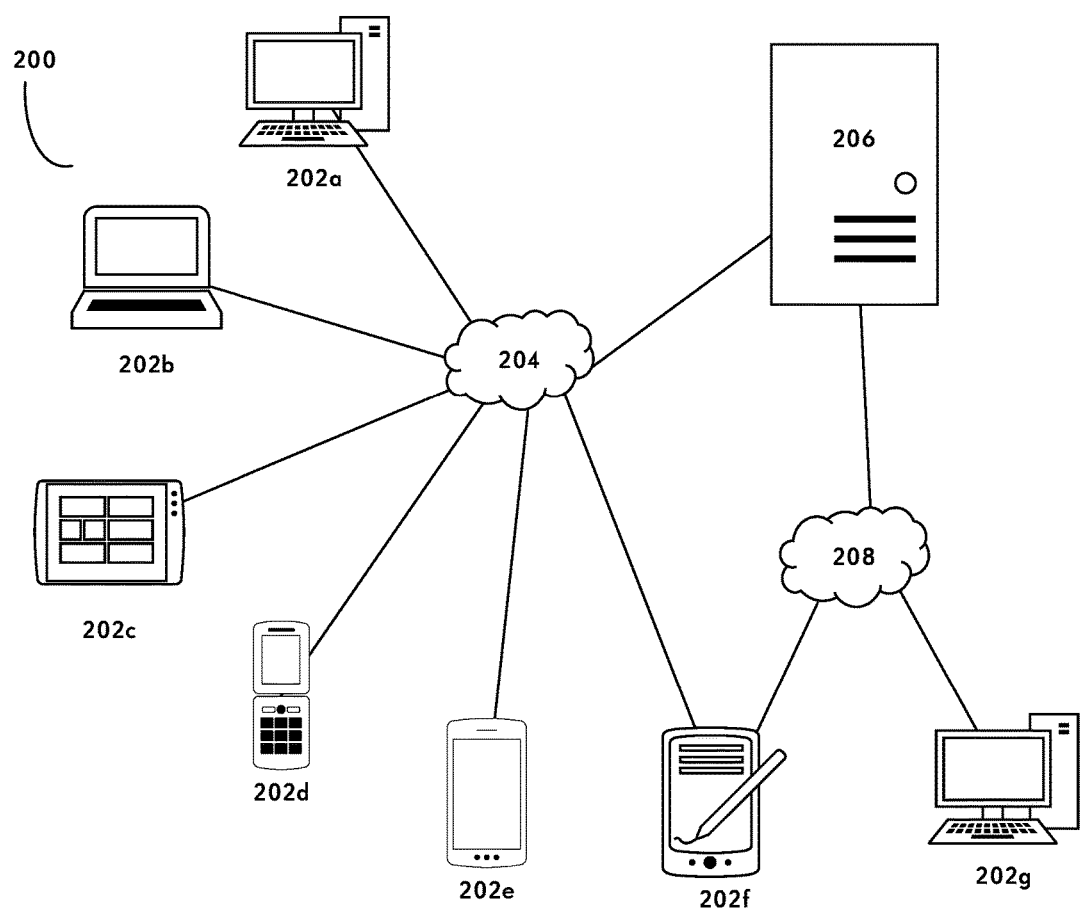

As noted above, portions of the variant storage system 100 may be distributed between one or more devices or components. FIG. 2 illustrates another embodiment of a variant storage system 200 according to the disclosure. In this embodiment, the variant storage system 200 comprises a plurality of client computing devices 202a-g, a network 204, and at least one server computing device 206. As shown, the client computing devices 202a-g may comprise desktop personal computers 202a, 202g, a laptop computer 202b, a slate device 202c, a mobile phone 202d, a smart phone 202e, and a tablet device 202f. Each client computing device 202a-g may communicate with other devices and computers via a network 204. The network 204 can be any network, such as the Internet, a wired network, a cellular network, and a wireless network. In certain embodiments, each client computing device 202a-g may communicate with one or more storage systems, server computing devices (e.g., the server computing device 206), cloud computing systems, or other sites, systems, or devices hosting external services to access remote data or remotely executing applications. Further, client computing devices 202a-g may utilize multiple networks to access the server computing device 206, such as a local connection 208. The local connection 208 may be, for example, a serial, USB, local area network (LAN), wireless, Bluetooth, or other form of local connection physically close in proximity to the server computing device 206.

Client computing devices 202a-g may be configured to receive information from the server computing device 206, such as encoded or decoded variant data and associated information. For example, the client devices 202a-g may access the server computing device 206 via an Application Programming Interface (API) over the network 204 which is configured to respond to requests for various content, and appropriately format the result.

In this embodiment, the server computing device 206 may be configured to encode, store, and decode variant data, similar to the computing device 102 of FIG. 1. Accordingly, the server computing device 206 may comprise a variant encoding engine and a variant decoding engine, such as the variant encoding engine 122 and variant decoding engine 124 of FIG. 1. Thus, each of the client computing devices 202 may connect to the server computing device 206 over the network 204 or local connection 208 in order to access variant data, encode variant data, decode variant data, or engage in some other form of interaction with the variant storage system 200. However, as noted above, various components of the variant storage system 200 may be implemented either partly or wholly within the client computing devices 202.

For example, in certain embodiments, the privacy of individuals in the population may be ensured by encoding variant data locally on a client computing device 202, as opposed to on the server computing device 206. Accordingly, all or portions of the variant encoding engine 122 and variant decoding engine 124 may be executed locally on the client computing devices 202. While the variant storage systems 100, 200 are described above as separate embodiments, various embodiments of variant storage systems 100, 200 may combine or interchange components to form various variant storage systems according to the disclosure. Further, the embodiments according to the disclosure may execute all or only parts of the exemplary methods and functions described herein. Various configurations and embodiments are considered to be within the scope of the disclosure.

Variant Encoding and Decoding Engines

Figure 3:
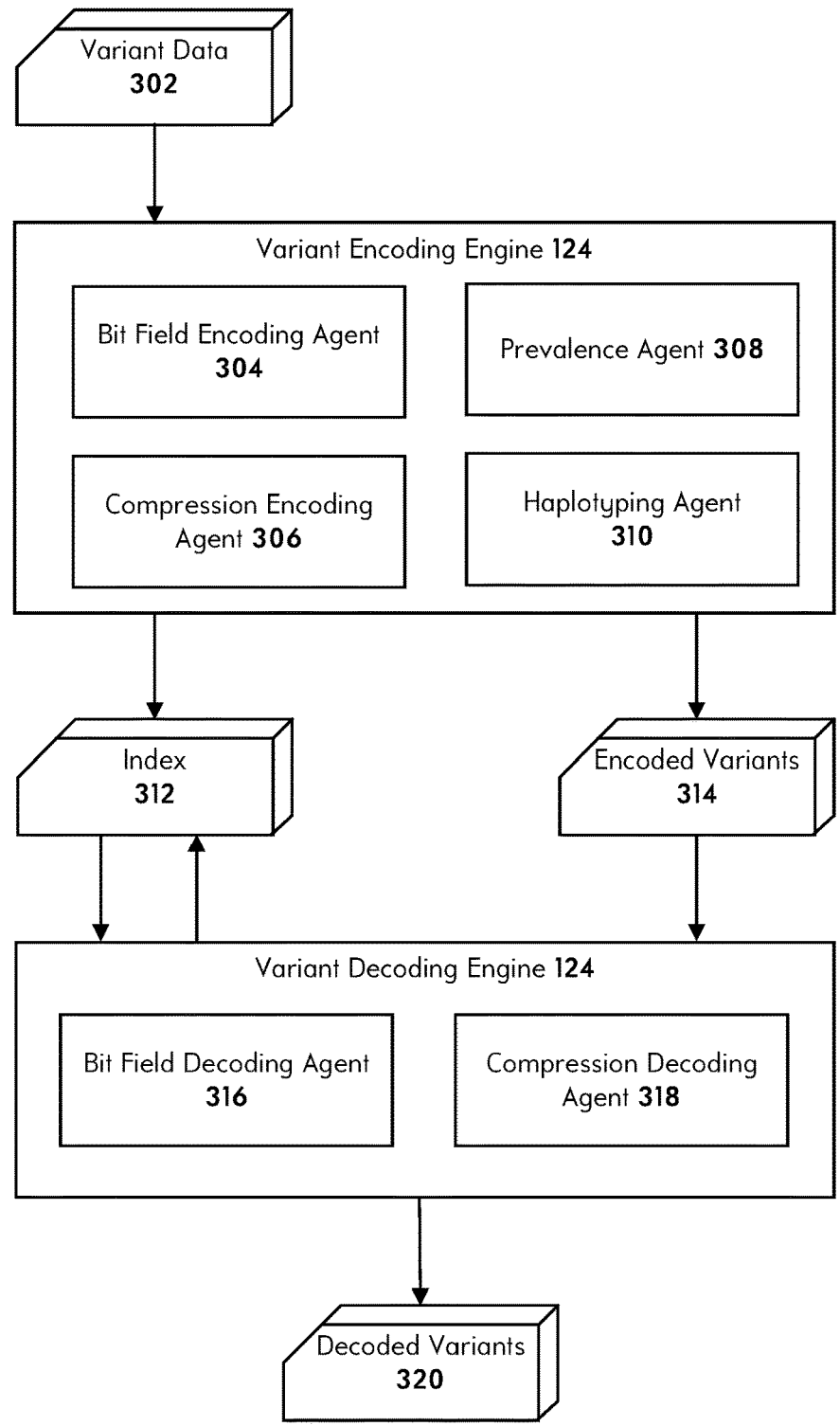

FIG. 3 illustrates the variant encoding engine 122 and variant decoding engine 124 of FIG. 1 in further detail. In this embodiment, the variant encoding engine 122 comprises a plurality of software routines or agents configured to perform functions associated with encoding variant data, such as a set of variants 302, for a population. For example, the variant encoding engine 122 can comprise a bit field encoding agent 304, a compression encoding agent 306, a prevalence agent 308, and a haplotyping agent 310. The bit field encoding agent 304 is configured to encode variants 302 as an array or field of bits. The compression encoding agent 306 is configured to encode variants 302 using a compression encoding scheme, such as run length encoding. The prevalence agent 308 determines the prevalence of each variant 302 in the population. The haplotyping agent 310 is configured to identify statistical associations between variants in the population and define sets of associated variants as haplotypes. As variants 302 are encoded by the variant encoding engine 122 into a set of encoded variants 314, information related to the method of encoding each variant (such as by the bit field encoding agent 304 and/or compression encoding agent 306) may be stored in the index 312. To decode the encoded variants 314, the variant decoding engine 124 may interact with the index 312 and encoded variants 314 by using a bit field decoding agent 316 and a compression decoding agent 318 to generate a set of decoded variants 320.

Variant data 302 may be provided to the variant encoding engine 122 in a variety of ways. For example, in certain embodiments, the variant encoding engine 122 may be configured to receive VCF or BCF files. Variant data set 302 may also be received or formatted by the variant encoding engine 122 as a two-dimensional space or table. The first dimension is the set of individuals in the population, and the other dimension is the set of variants. Each intersection describes the genotype of an individual with respect to that variant, i.e., the presence or absence of a particular sequence in that individual's genome. In certain embodiments, each variant can be described as a vector or array of genotypes for a plurality of individuals. In other embodiments, each individual can be described as a vector or array of genotypes for a plurality of variants.

Instead of storing actual nucleotide sequence information, genotypes can be expressed as differences from the reference genome, thus making it easier to store and compress data. For example, "0" can represent the reference nucleotide sequence in the reference genome for that variant, "1" can represent a first allele, "2" can represent a second allele, and "3" can represent a third allele. As there are only four possible nucleotides (A, C, G, T, excluding other ambiguity symbols), typically only four alleles (including the reference nucleotide sequence) are possible at a particular variant position. However, there may be situations in which there are more than four alleles, such as for variants including short insertions or deletion events, or for structural variants. (Often these variants may simply be included as a new variant in a data set, rather than defining additional alleles.)

For the human genome, each individual in a population has two copies of each chromosome, and thus the genotype for an individual requires the characterization of the variant for both chromosomes. If each variant has a maximum of four alleles, the characterization of a variant on one chromosome (a haploid) can be expressed by two bits, i.e., $\Sigma \in \{0, 1, 2, 3\}$. Similarly, an un-phased genotype can be expressed as a pair of haploid values, requiring four bits, i.e., $\Sigma \in \{0/0, 0/1, 0/2, 0/3, 1/1, 1/2, 1/3, 2/2, 2/3, 3/3\}$. Genotypes may be phased or un-phased. Phasing refers to knowledge as to the particular chromosome in which a variant is present. If un-phased, then the genotypes "1/0" and "0/1" are essentially identical and may be collapsed (as in the above representation). However, if phased, these genotypes are unique and should be accounted for in the representation. For phased data, genotypes can require additional bits as there may be up to 16 possible genotypes given four potential alleles, i.e.:

$\Sigma \in \{0|0, 0|1, 0|2, 0|3, 1|0, 1|1, 1|2, 1|3, 2|0, 2|1, 2|2, 2|3, 3|0, 3|1, 3|2, 3|3\}$, which would require five bits. As shown above, the "/" symbol is commonly used to represent un-phased data, whereas a "|" symbol is used to represent phased data (e.g., in VCF format). Of course, systems and methods according to the disclosure may operate using either phased or un-phased data.

In addition to pairs of values representing an allele for each chromosome, genotypes can also be stored or expressed as a single value, which represents the ten possible un-phased diploids from two haploids, which also requires four bits: $\Sigma \in \{0 \ldots 10\}$. As previously noted, regardless of the representation used, genotypes may be stored in a two-dimensional space in which the individuals are expressed along a first dimension and the variants are expressed along a second dimension. For example, the variant table below describes the status of 15 individuals $\{P_1 \ldots P_{15}\}$ for 15 variants $\{V_1 \ldots V_{15}\}$ using a diploid representation of each un-phased genotype. In certain embodiments, the variant encoding engine 122 may convert received variant information into this format (e.g., after receiving a VCF or BCF file).

Bit Field Encoding of Variants

The bit field encoding agent 304 is configured to encode the variants 302 as an array of bits, i.e., by using a bit field encoding scheme. In certain embodiments, the bit field encoding scheme may comprise representing variants as a minimal number of bits. For purposes of the disclosure, bit field encoding is a way to represent and store multiple bits in memory such that single bits can be addressed. For example, a bit field in the C++ programming language is a data structure having several labelled fields, each of which can be set, tested, or changed using a mask or bitwise operators. Each variant can thus be stored as a bit field and stored and accessed when needed.

Variants may be bit field encoded along either the variant dimension or along the people dimension. When encoding along the variant dimension (i.e., representing each variant as an array of genotypes for a plurality of individuals), the number of bits required for a particular variant may vary depending on its type and the number of possible alleles. For example, 95% of variants identified by The 1000 Genomes Project are SNPs, and of these, 95% are bi-allelic, meaning that there is only one known variation from the reference, and thus there are only two potential alleles. For bi-allelic SNPs, only 1 bit per haploid is required (0 or 1), and 2 bits per diploid (00, 01, 10, or 11). For example, the V7 variant in Table 1 is a bi-allelic variant having only two alleles, and thus can be encoded using only two bits per entry:

V7: 01 11 10 01 10 10 11 01 11 01 01 01 01 10 01 10, which requires only 30 bits. However, the V8 variant is tri-allelic, including at least two individuals that possess the additional allele. Representing this variant using bit field encoding (and un-phased genotypes) may require at least three bits per entry:

V8: 010 010 010 001 000 010 010 010 001 100 010 001 000 100 010

(which requires 45 bits). However, as the vast majority of variants are bi-allelic, variants such as V8 will not substantially increase the total number of bits required for the population. The bit field encoding agent 304 may store the number of bits required for each variant in a database or an index, such as the index 312. Similar bit-efficient strategies for encoding each variant could be employed, such as Huffman coding, for example. BCF, in contrast, would require 240 bits (16 bits per genotype for 15 individuals) to encode either the V7 or V8 variants.

In certain embodiments, methods and systems according to the disclosure may encode a variant set for a population

TABLE 1

Exemplary Variant Set

| | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ | $V_{14}$ | $V_{15}$ |
|---|---|---|---|---|---|---|---|---|---|---|---|---|---|---|---|
| $P_1$ | 0 | 0 | 0 | 0 | 1 | 2 | 1 | 2 | 0 | 0 | 2 | 2 | 1 | 0 | 0 |
| $P_2$ | 0 | 0 | 0 | 0 | 1 | 1 | 3 | 2 | 0 | 0 | 1 | 2 | 0 | 3 | 0 |
| $P_3$ | 0 | 0 | 0 | 0 | 1 | 1 | 2 | 2 | 0 | 0 | 0 | 0 | 2 | 2 | 0 |
| $P_4$ | 0 | 0 | 0 | 0 | 1 | 2 | 1 | 1 | 0 | 0 | 0 | 2 | 1 | 3 | 0 |
| $P_5$ | 0 | 0 | 0 | 0 | 0 | 2 | 2 | 0 | 0 | 0 | 1 | 2 | 1 | 3 | 0 |
| $P_6$ | 0 | 0 | 0 | 0 | 0 | 2 | 2 | 2 | 0 | 0 | 2 | 3 | 0 | 3 | 0 |
| $P_7$ | 0 | 0 | 0 | 0 | 0 | 2 | 3 | 2 | 0 | 0 | 1 | 0 | 2 | 1 | 0 |
| $P_8$ | 0 | 0 | 0 | 0 | 1 | 0 | 1 | 2 | 0 | 0 | 2 | 0 | 1 | 2 | 0 |
| $P_9$ | 0 | 0 | 0 | 0 | 1 | 2 | 3 | 1 | 0 | 0 | 1 | 1 | 2 | 1 | 0 |
| $P_{10}$ | 0 | 0 | 0 | 0 | 1 | 2 | 1 | 4 | 0 | 0 | 1 | 1 | 2 | 2 | 0 |
| $P_{11}$ | 0 | 0 | 0 | 0 | 1 | 2 | 1 | 2 | 0 | 0 | 0 | 2 | 1 | 1 | 0 |
| $P_{12}$ | 0 | 0 | 0 | 0 | 2 | 2 | 1 | 1 | 0 | 0 | 1 | 2 | 1 | 3 | 0 |
| $P_{13}$ | 0 | 0 | 0 | 0 | 2 | 2 | 2 | 0 | 0 | 0 | 2 | 0 | 1 | 2 | 0 |
| $P_{14}$ | 0 | 0 | 0 | 0 | 0 | 1 | 1 | 4 | 0 | 0 | 2 | 0 | 2 | 1 | 0 |
| $P_{15}$ | 0 | 0 | 0 | 0 | 0 | 2 | 2 | 2 | 4 | 4 | 0 | 1 | 2 | 2 | 0 | using only bit field encoding. Bit field encoding techniques according to the disclosure have a great storage improvement over conventional formats, such as BCF. For example, the full set of variants from The 1000 Genomes Project, stored using uncompressed BCF, requires 378 gigabytes of storage space. In contrast, the use of a bit field encoding scheme according to the disclosure results in a storage requirement of only 47.2 gigabytes, with similar speed in access times and low overhead cost.

Run Length Encoding of Variants

The compression encoding agent 306 is configured to encode the variants 302 using a compression encoding scheme, such as run length encoding. Run-length encoding is an effective way of compressing data in a way this is easily restorable, and further has the virtue of efficient iteration over a sequence. Run length encoding may be understood as a scheme in which stretches of a particular value (i.e., a "run") are replaced by a single instance of the value, followed by a value representing the length of the stretch. In this way, run-length encoding exploits coherence in a data set. It is particularly effective for storing large sequences that frequently consist of only one value, such as population variant data. Greater storage efficiency is achieved when there is high coherence, such as when most of the population has the same genotype. Run-length encoding can be performed by either encoding each individual as a sequence of N variants (i.e., $V_1, V_2, \ldots V_N$), or by encoding each variant as a sequence of K individuals (i.e., $P_1, P_2, \ldots P_K$).

To encode a set of variants using run length encoding, the compression encoding agent 306 could process each row of a variant set (such as the variant set in Table 1, above) listing the genotypes of a plurality of individuals and identify instances where a particular genotype is followed by the same genotype. The compression encoding agent 306 could then determine, for each of the instances, a run length, i.e., the number of times the particular genotype has been repeated in the instance. Instances having a run length of more than a predetermined value (e.g., 4) can be identified by the program as continuous stretches of similar genotypes. The compression encoding agent 306 subsequently replaces the identified stretches with a single instance of the genotype followed by the associated run length. Similarly, the compression encoding agent 306 could instead process each column and encode a plurality of genotypes for each variant.

Further, if instances of run lengths are less than a certain value, a run length encoding entry (i.e., instance and run length) may be less efficient than simply storing the values themselves. In these cases, the values may simply be stored unmodified, or using bit field encoding.

Run Length Encoding Over Variants

As previously noted, one way to run length encode variant data is to encode a sequence of genotypes for the individuals in the population for that variant. To improve the efficiency of run length encoding in this manner, variants may first be sorted by allele frequency. For example, about 95% of known variants are extremely rare within a population. Run length encoding efficiencies can be improved by sorting variants such that those of low prevalence are shifted to one edge of the table. Sorting the variants in Table 1 above by their prevalence, or frequency within the population, shifts the rare variants in the table to the left, as shown in Table 2, below:

TABLE 2

Variant Set Sorted by Prevalence

| | $V_1$ | $V_2$ | $V_3$ | $V_4$ | $V_{15}$ | $V_9$ | $V_{10}$ | $V_5$ | $V_{11}$ | $V_{12}$ | $V_{13}$ | $V_8$ | $V_6$ | $V_7$ | $V_{14}$ |
|---|---|---|---|---|---|---|---|---|---|---|---|---|---|---|---|
| $P_1$ | 0 | 0 | 0 | 0 | 0 | 0 | 0 | 1 | 2 | 2 | 1 | 2 | 2 | 1 | 0 |
| $P_2$ | 0 | 0 | 0 | 0 | 0 | 0 | 0 | 1 | 1 | 2 | 0 | 2 | 1 | 3 | 3 |
| $P_3$ | 0 | 0 | 0 | 0 | 0 | 0 | 0 | 1 | 0 | 0 | 2 | 2 | 1 | 2 | 2 |
| $P_4$ | 0 | 0 | 0 | 0 | 0 | 0 | 0 | 1 | 0 | 2 | 1 | 1 | 2 | 1 | 3 |
| $P_5$ | 0 | 0 | 0 | 0 | 0 | 0 | 0 | 0 | 1 | 2 | 1 | 0 | 2 | 2 | 3 |
| $P_6$ | 0 | 0 | 0 | 0 | 0 | 0 | 0 | 0 | 2 | 3 | 0 | 2 | 2 | 2 | 3 |
| $P_7$ | 0 | 0 | 0 | 0 | 0 | 0 | 0 | 0 | 1 | 0 | 2 | 2 | 2 | 3 | 1 |
| $P_8$ | 0 | 0 | 0 | 0 | 0 | 0 | 1 | 2 | 0 | 1 | 2 | 0 | 1 | 2 | |
| $P_9$ | 0 | 0 | 0 | 0 | 0 | 0 | 1 | 1 | 1 | 2 | 1 | 2 | 3 | 1 | |
| $P_{10}$ | 0 | 0 | 0 | 0 | 0 | 0 | 1 | 1 | 1 | 2 | 4 | 2 | 1 | 2 | |
| $P_{11}$ | 0 | 0 | 0 | 0 | 0 | 0 | 1 | 0 | 2 | 1 | 2 | 2 | 1 | 1 | |
| $P_{12}$ | 0 | 0 | 0 | 0 | 0 | 0 | 2 | 1 | 2 | 1 | 1 | 2 | 1 | 3 | |
| $P_{13}$ | 0 | 0 | 0 | 0 | 0 | 0 | 2 | 2 | 0 | 1 | 0 | 2 | 2 | 2 | |
| $P_{14}$ | 0 | 0 | 0 | 0 | 0 | 0 | 2 | 0 | 2 | 4 | 1 | 1 | 1 | | |
| $P_{15}$ | 0 | 0 | 0 | 0 | 4 | 4 | 0 | 0 | 1 | 2 | 2 | 2 | 2 | 2 | |

Each row in Table 2 may then be run length encoded, for example, by identifying instances within the row in which a value is followed by several copies of the same value. A run length entry may then be created to represent the value and the number of times it is repeated. In certain embodiments, a run length entry may comprise two bytes, wherein the first byte represents the value and the second byte represents the run. For example, run-length encoding any sequence of more than four identical symbols in Table 2 above yields the following encoded representation (with the run length entries in bold):

P1: 0(7)12212210
P2: 0(7)11202133
P3: 0(7)10022122
P4: 0(7)10211213
P5: 0(7)01210223
P6: 0(7)02302223
P7: 0(7)01022231
P8: 0(7)12012012
P9: 0(7)11121231
P10: 0(7)11124212
P11: 0(7)10212211
P12: 0(7)21211213
P13: 0(7)22010222
P14: 0(7)02024111
P15: 0(5)440012 (5)

Run length encoding in this manner can greatly reduce the storage space required for representing variant data. For example, empirical testing using unsorted variants from the 1000 Genomes Project over chromosome 22 resulted in run length entries varying between 61,627 and 90,455 per individual, for a total of 367,568,792 run length entries for the population. Using 2-byte run length entries (i.e., one byte representing the value and one byte representing the run), the total size required for storage was 735 megabytes.

Run Length Encoding over Individuals

Another approach is to run length encode the genotypes of a plurality of individuals for each variant (i.e., in the variant tables above, run length encode each column). Run length encoding over individuals is extremely efficient and can take advantage of inherent properties of the data set without any additional sorting. For example, the variant set in Table 1 would yield the following representation if any runs of four or more are encoded using run length encoding:

V1: 0(15)
V2: 0(15)
V3: 0(15)
V4: 0(15)

V5: 1(4)0001(4)2200
V6: 2112(4)02(5)12
V7: 132122313111212
V8: 222102221421042
V9: 0(14)4
V10: 0(14)4
V11: 210012121101220
V12: 220223001122001
V13: 102110212211122
V14: 032333121213212
V15: 0(15)

As shown by the above representation, certain variants (such as those that are rare in the population) run length encode extremely well, but other, more common, variants do not. For example, in empirical testing over chromosome 22 using variants from the 1000 Genomes Project, the number of run length entries was between 1 and 5006, with the $90^{th}$ percentile at 460, for a total of 191,105,351 run length entries. Using 2-byte run length entries, the total size required for storage was 382 megabytes, a nearly 100% improvement compared to run length encoding over variants. In another empirical analysis, run length encoding over individuals for the entire 1000 Genomes data set resulted in a file size of only 26 gigabytes, compared to 47.2 gigabytes for bit field encoding. Moreover, no sorting is required to achieve these results, as the inherent characteristics of the data set itself result in efficient run length encoding. Accordingly, the present disclosure recognizes that run length encoding over individuals is more efficient than run length encoding over variants; the number of run length entries is decreased, with a corresponding increase in the run lengths themselves.

Further, it should be noted that run length encoding over variants and sorting of variants based on prevalence leads to the loss of important information that can be exploited to further efficiently encode the variant data. For example, due to the linkage disequilibrium effect, variants positioned on the same chromosome and positioned close to one another may have alleles that are statistically associated with one another. This information is useful and can be used to further efficiently encode data, such as by exploiting the presence of haplotypes, i.e., variants on the same chromosome with alleles that often occur together (described in further detail below). Run length encoding over individuals by ordering variants based on their position on the chromosome preserves this information, while allowing for the long stretches of continuous sequence to be efficiently stored.

In this embodiment, the compression encoding agent 306 uses run length encoding. Run length encoding is particularly suited for variant data due to a small alphabet and the presence of long runs of like symbols. However, in other embodiments other compression schemes may be used. For example, in certain embodiments, Lempel-Ziv-Welch (LZW) compression, GZIP compression, or other compression formats may be used. Similarly, hybrid approaches may be used, such as Word-Aligned Hybrid (WAH) encoding. Various embodiments are considered to be within the scope of the disclosure.

Efficiencies of Encoding Schemes can Depend on Genotype Representation

As previously noted, genotypes can be represented as either a pair of values (such that each value represents the status of a variant with respect to one chromosome) or as a single value (representing the status of an allele on both chromosomes). In practice, representing genotypes using pairs tends to lead to improved run length encode better, whereas using single values is more bit efficient for variants with multiple alleles, and for un-phased variants with multiple alleles and defined haplotypes (i.e., groups of variants encoded together due to statistical associations present in the data, as described herein). Systems and methods according to the disclosure may use either representation.

Other Elements

The index 312 may be used to store information related to the encoding scheme used for a variant. For example, in certain embodiments, various encoding schemes or modifications to encoding schemes may be employed for each variant to maximize storage and access efficiency. The index 312 may thus be consulted (e.g., by the variant decoding engine 124) to determine how to identify a representation of the data for decoding. The index 312 may also be used to store information associated with a variant, such as various metadata, position within the reference genome, whether the variant is known to be associated with cancer, and the like. In certain embodiments, the index 312 may be stored on a storage device or in a database, such as the storage device 114 and database 120 of FIG. 1.

The prevalence agent 308 is configured to analyze characteristics of the variant data 302 that may be used to efficiently encode the data set. For purposes of the disclosure, the term "prevalence" refers to the frequency at which alternate alleles of a given variant occur in the population. For example, the majority of variants in a population are relatively rare and therefore not prevalent. In one study, nearly 64 million autosomal variants were observed in less than 0.5% of the population, 12 million (15%) were observed in between 0.5% and 5% of the population, and only 8 million (10%) had a frequency in excess of 5%. See The 1000 Genomes Project Consortium, "A global reference for human genetic variation", *Nature;* 526(68) (2015). The prevalence agent 308 can be configured to determine whether a given variant is relatively common or rare in the population. Prevalence can be measured in a variety of ways, including the number of run length entries required to encode a variant, the number of observations of alternate alleles of the variant in the population, or the variability of observed alleles.

The haplotyping agent 310 is configured to analyze and identify statistical associations between variants in the variant data set that can be leveraged to efficiently encode the data. Due to phenomena such as linkage disequilibrium, population data sets exhibit non-random statistical associations between variants at different locations that are different from what would be expected if the alleles were independently and randomly sampled. For example, a set of variants in five individuals may have up to 96 possible combinations; however, in the actual data set, only 5 combinations may actually exist. As will be described in further detail below, each actual combination may be associated with a single value, and this information may be subsequently stored in the index 312.

Finally, the variant encoding engine 122 outputs the set of variants 302 as a set of encoded variants 314. The encoded variants 314 occupy substantially less storage space than would be required using other formats, and thus allow for meaningful research and analysis using only commodity hardware, such as a laptop, for example. Encoded variants 314 may be stored locally on the computing device 102 or storage device 114, such as in a database 120, for example. However, in other embodiments, encoded variants 314 may be stored or accessed from other devices and accessed over a network, for example.

Once a set of variants 302 has been encoded, they may subsequently be decoded by the variant decoding engine

124. As shown in this embodiment, the variant decoding engine 124 further comprises a bit field decoding agent 316 and a compression decoding agent 318, which can be used to decode those variants encoded as a bit field or as a series of run-lengths, respectively. While not shown in this embodiment, the variant decoding engine 124 may comprise additional agents to decode variants encoded using other means (such as those encoded as haplotypes or using alternate compression schemes, for example). The variant decoding engine 124 can query the index 312 to identify a location in memory or storage for a variant, select an appropriate decoding scheme, and subsequently decode the variant, resulting in a set of decoded variants 314.

While in this embodiment, the variant encoding engine 122 comprises the bit field encoding agent 304, compression encoding agent 306, prevalence agent 308, and haplotyping agent 310, in certain embodiments various agents may be omitted or additional agents may be added. For example, in certain embodiments, only a bit field encoding scheme may be used; in other embodiments, only a run length encoding scheme may be used. Similarly, the variant decoding engine 124 can comprise only those agents necessary for appropriately decoding the encoded variants 320.

II. Exemplary Variant Encoding Methods

As previously noted, embodiments according to the disclosure may use various encoding techniques to efficiently encode variant information for a population. In certain embodiments, an encoding scheme may be chosen for each variant based on characteristics of that variant within the population. For example, for highly prevalent variants within the population, a variant may be more efficiently encoded using a first encoding scheme, such as a bit field encoding scheme. However, for those variants that are rare, a second encoding scheme, such as a run length encoding scheme, may be substituted. In this way, embodiments according to the disclosure uniquely leverage properties that emerge from the variant data when it is considered in the context of a large population, allowing for the efficient encoding and decoding of variant data at extremely large scales.

Figure 4:
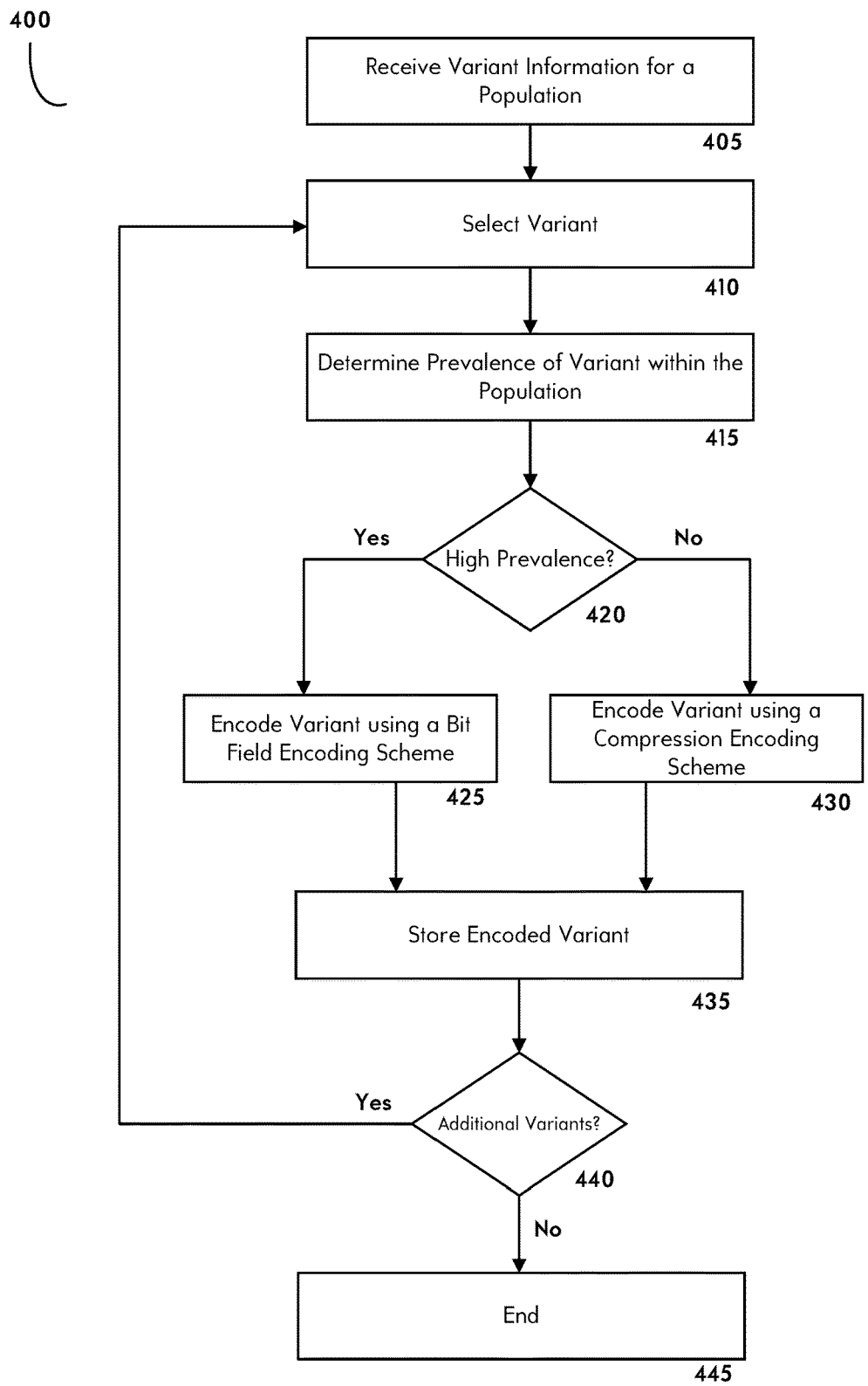

FIG. 4 is a flow diagram illustrating an exemplary embodiment of a method 400 of encoding a plurality of variants for a population. The method 400 may be performed in the context of a variant storage system 100, and practiced at least in part by a variant encoding engine 122, for example. Based on a set of variants for a population, the method 400 identifies a profile for encoding that minimizes the amount of storage space required for each variant. The method 400 may begin by receiving (e.g., by a variant encoding engine 122) a plurality of variants for a population (step 405). The variant encoding engine 122 may then select a variant (step 410) and determine the prevalence of that variant within the population (step 415). If the variant has a high prevalence in the population (decision 420), then it may be encoded using a first encoding scheme, such as a bit field encoding scheme (step 425). However, if the variant has a low prevalence, then the variant encoding engine may instead encode the variant using a second encoding scheme, such as a compression encoding scheme (such as run length encoding) (step 430). Once encoded, the variant may be stored (step 435) such that it may be accessed and decoded at a later time. The method 400 then proceeds by determining whether there are additional variants (decision 440), such that each variant is encoded based on its prevalence within the population. If there are no additional variants, the method 400 may then complete (step 445).

Receiving variant information (step 405) can be performed in a variety of ways. As previously noted, variants may be provided to the variant encoding engine 122 as one or more VCF or BCF files. Additional formatting may be performed on variant information once it is received. For example, variant information may be formatted to be expressed as a two-dimensional space. The first dimension is each individual in the population, and the second dimension is each variant. Each intersection between the individuals and variants describes the genotype of an individual with respect to that variant, i.e., the presence or absence of a particular sequence in that individual's genome. A variant may be expressed as a sequence of symbols describing the genotypes of a plurality of individuals for that variant.

Variants may then be selected for encoding (step 410), and their prevalence within the population determined (step 415). The prevalence of a particular variant is related to the genetic diversity shown by the population. Populations of individuals exhibit genetic diversity, which refers to the variability of characteristics in the genetic makeup of a species. Genetic diversity is the result of the accumulation of random mutations within a population over long periods of time. In nature, genetic diversity serves as a way for populations to adapt to changing environments. When a population has a large amount of variation, it is likely that some individuals in the populations possess variations of alleles that are best suited for a new environment. In turn, these individuals will be more likely to survive, thus producing offspring bearing that allele and increasing the prevalence of that allele in the population.

Highly common variations observed in the human population include those that determine the color of one's hair, skin, and eyes; the likelihood as to whether an individual will enjoy the taste of cilantro; and how the body reacts when digesting certain foods, such as asparagus. Variations such as these encode for the majority of observable diversity present in the population. However, the vast majority of identified variants in the human population are relatively rare. These relatively rare variants often show no phenotype and can be entirely harmless. Others may be related to degenerative diseases, such as Parkinson's disease and Cystic Fibrosis. Still less common variations will be those that occur de novo within an individual due to mutagenesis; in certain cases, only one individual in a population will possess these variants. By selecting an encoding scheme according to a variant's prevalence within the population, systems and methods according to the disclosure are able to maximize storage efficiency As previously noted, prevalence refers to the variability of genotype data for variants within a population. A variant that is prevalent, i.e., exhibits high variability within the genotype data across individuals in the population, describes a mutation within the genome that is frequently observed across the population. The prevalence of a variant within the population may be determined (step 415) in a variety of ways. For example, prevalence can refer to the frequency at which alternate alleles of a variant are observed in the population. Because high prevalence indicates high variability within the variant data, a run length encoding scheme is not ideal. Accordingly, in certain embodiments, the number of run length entries required to run length encode a variant may be a measure of prevalence. Variants requiring a large number of run length entries are considered prevalent, whereas variants with only a few are not prevalent. In particular, the storage space required for a certain number of run length entries may be compared to that required for a bit field encoding scheme; if bit field encoding would require less storage space, then it may be substituted for that variant.

Further, the vast majority of variants are relatively simple. For example, 95% of variants identified by the 1000 Genomes Project are single nucleotide polymorphisms (SNPs). Of these SNPs, 95% exhibit only one known variation from the reference sequence, and thus there are only two possible alleles for the variant: the reference and the variation; i.e., the variants are bi-allelic. This property can be leveraged to efficiently encode variation data for a population. At a minimal level, bi-allelic variants require only one bit per chromosome (0 or 1), and two bits per genotype (00, 01, 10, 11). Other more complex variants may require additional bits. For example, in the embodiment of the un-phased diploid encoding representation previously described (and exemplified in Table 1), genotypes for variants having more than two alleles may require up to four bits per genotype. However, as these variants are typically in the minority of the variant set, they will not substantially increase the total number of bits required to represent and store variants for the entire population.

If a given variant has high prevalence, the variant will be more efficiently stored (i.e., require less storage space) using a bit field encoding scheme (step 425). As previously noted, in certain embodiments, the bit field encoding scheme may comprise representing a variant as an array, vector, or sequence of bits. Further, in certain embodiments, the bit field encoding scheme may comprise representing the variant as a minimal number of bits. While remarkably efficient compared to uncompressed BCF, bit field encoding does not take advantage of other properties of large variant stores that can be used for efficient encoding. For example, most variants are relatively rare in a population. In these cases, the majority of individuals have a value of "0" stored for these variants, meaning that these individuals have no deviation from the reference sequence. This results in long runs of "0" in the data set, which can best be exploited using a run length encoding scheme. Accordingly, if the method 400 determines that the variant has low prevalence (decision 420), the variant may instead by encoded using a compression encoding scheme (step 430), such as run length encoding.

One way to determine which encoding format to use is to simply perform both on a variant and select the scheme that is superior. For example, one could perform both bit field encoding and run length encoding for a variant. If the number of run length entries generated results in a required storage space in excess of that needed for bit field encoding, bit field encoding may be preferable for that variant. Thus, in certain embodiments, an encoding scheme may be chosen by performing a first encoding technique (such as run length encoding), and rejecting it unless it is smaller than the representation using a second encoding technique (such as bit field encoding).

Once the variant has been encoded based on its prevalence within the population, it may be stored for later access. The encoded variant may be stored on a storage device having a database, such as the storage device 114 and database 120 of FIG. 1. Additional variants (decision 440) may subsequently be selected and encoded in a similar fashion. Once all variants have been encoded, the method may complete (step 445).

While run length encoding can be better overall than bit field encoding for encoding variant data for a population, there are local situations where either technique may be preferable. For example, as shown above, certain variants may run length encode over individuals very well, but other more prevalent variants do not. In these cases, variants can be efficiently encoded by choosing an encoding scheme optimized for the characteristics of that variant. In particular, further improvements to the efficient encoding of variants can be made by switching the encoding scheme depending on whether run length encoding or bit field encoding is more efficient.

This determination can be made in a variety of ways. For example, run length encoding works well in regions of high coherence, and thus can be applied to the majority of a population data set because the vast majority of variants are very rare. For example, 92.1% of variants on human chromosome 22 are seen in less than 10% of the population; 90.1% are seen in less than 5%; 83.3% are seen in less than 1%; and 64.8% are seen in less than 0.1%. However, more common variants will not gain any benefits, or may even negatively impact a run-length encoding scheme. For example, as shown above, certain variants run length encode very well, but others do not due to their prevalence in the population. Accordingly, these variants can be encoded using bit field encoding.

Figure 5:
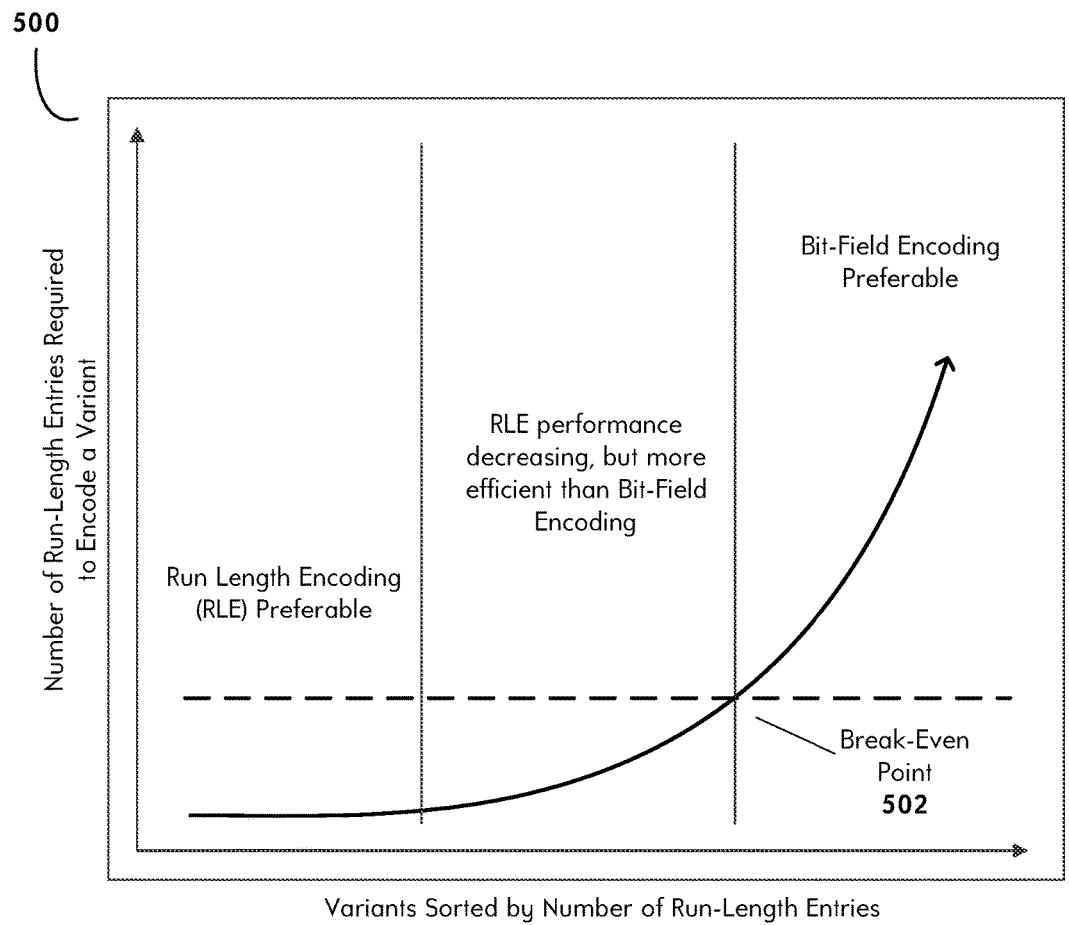

FIG. 5 is a chart 500 depicting a relationship between the prevalence of variants in a data set and the choice of an encoding scheme. In the chart 500, variants have been sorted by the number of run length entries required to encode the variants. As variants become more common (and thus require additional run length entries to encode), bit field encoding eventually meets and then exceeds the performance of run length encoding, e.g., at a break-even point 502. Thus, the encoding strategy can be switched at this break-even point 502.

According to experimental data using 2-byte (16 bit) run length entries and the 1000 Genomes Project data set, the number of run length entries per variant for which bit field encoding becomes more efficient is about 313. For chromosome 22, 88.4% of variants were found to encode more efficiently using 16 bit run length entries, with a resulting data set comprising 42.3 megabytes for run length encoded variants, and 81.3 megabytes for bit field encoded variants, totaling 127.3 megabytes for chromosome 22. When expanded to the 1000 Genomes Project data set, the resulting storage space required is reduced from 26 gigabytes (for pure run length encoding) to 8.45 gigabytes for an adaptive model. Of course, in certain embodiments, the break-even point 502 can vary depending on the type of encoding strategies used.

Further, the foregoing should hold true as the population size grows. As the population set gets very large, it is more likely that new variants will be rare, as any common variants are more likely to already be represented in the data set. Thus, as the population in a data set grows, nearly all new variants will be encoded using run length encoding.

Use of Variable Bit Formats for Run Length Encoding

In certain embodiments, run length encoding may further comprise the use of variable bit formats to further improve efficiency. For example, there is no need for all values to have uniform run length entries; rather, the run length encoding scheme can be variable and only use the number of bits required to store both the genotype and its associated run length. This can be exploited in the following manner. In the 1000 Genomes Project variant set for chromosome 22, 99.997% of runs of "0" have an associated run length of less than 2,000. This can be encoded with a 12-bit format, which uses 1 bit to represent the variant and 11 bits to represent the run length (which allows for a run of up to 2,048). Similarly, 99.98% of runs of "1" have a run length between 1 and 7. This can be efficiently encoded with a 4-bit format, which uses 1 bit to represent the variant and only 3 bits to represent the run length. (Of course, a variable bit format may also be used for compression schemes other than run length encoding.)

In certain embodiments, optimal run length formats may be determined for each variant individually. Further, it should be noted that a final "zero" allele (i.e., genotypes representing the reference sequence) run length entry for a given variant is redundant as it can be inferred from the data. Removing this entry represents a possible significant percentage of space saving. Systems and methods according to the disclosure may implement corresponding logic in order to make this determination; for example, a modified run length entry could be used, or the simple absence of a final run length entry could indicate that the remaining genotypes are the reference allele.

The use of variable bit formats for run length encoding may affect the break-even point 502. For example, using these modifications, variants of up to 625 run length entries (an increase from 311) can be more efficiently encoded using run length encoding as opposed to bit field encoding. This is because 91.2% of variants code more efficiently using the 12/4 bit run length entries. In an empirical analysis using variants for chromosome 22 from the 1000 Genomes Project data set, 34.4 megabytes can be used for run length encoding and only 57.9 megabytes for bit field variants, requiring only 92.3 megabytes for storage. Expanded to the full 1000 Genomes Project data set, the use of variable bit formats for run length encoding results in an additional storage reduction from 8.45 gigabytes to 6.56 gigabytes. Information regarding the bit format used for each variant may be stored in an index and later accessed by a decoder, such as the index 312 and variant decoding engine 124 of FIG. 3.

Exploiting Statistical Associations between Variants

Due to phenomena such as linkage disequilibrium, many variants and their alleles when considered in the context of large populations occur together with some statistical significance. In particular, there are statistical associations between alleles at different loci than what would be expected if the alleles were independently and randomly sampled based on their individual allele frequencies. This is particularly evident in typical short segments of chromosomes, in which there are usually only a few distinct haplotypes. Careful selection of individual variants can thus be used to determine the status of other variants. This property can be exploited to achieve additional efficiencies in both access speed and storage of variant data.

For example, consider a set of phased variants. Each variant has a given number of alleles and so, for a set of N variants, there are $\Pi_{n=0}^{N} \text{NumAlleles}_n$ combinations of the alleles of those variants. However, in most cases, a population typically only exhibits a small subset of those combinations. For example, consider a set of five variants $\{V_1 \ldots V_5\}$ for five groups of individuals $\{G_1 \ldots G_5\}$ in Table 3, below. $V_1$ has two possible alleles; $V_2$ has three; $V_3$ has one; $V_4$ has four; and $V_5$ has two. The total number of possible combinations of these alleles that may be present in a large population due to chance is 96 (2*3*2*4*2), requiring a minimum of 6*2=12 bits per allele to encode. However, due to non-random associations between the alleles, in the actual population, only 5 combinations of these alleles (i.e., those combinations shown by Groups 1-5) actually exist in the population. For 5 combinations, only 3*2=6 bits of data are required for the representation. Thus, each of the 5 unique combinations can be replaced by a single meta-variant, or "haplotype" (H) having allele values that map to a table of variant allele values. Each defined haplotype represents a set of variants associated with one another. In the representation, the variants are simply replaced with their meta-variant or haplotype value, and an additional lookup may be performed to determine the status of the variants in that haplotype. The haplotyped values may similarly be run length or bit field encoded in accordance with other embodiments of the disclosure.

TABLE 3

|       | $V_1$ | $V_2$ | $V_3$ | $V_4$ | $V_5$ |    | H |
|-------|-------|-------|-------|-------|-------|----|---|
| $G_1$ | 0     | 0     | 0     | 1     | 0     | -> | 0 |
| $G_2$ | 1     | 1     | 0     | 2     | 0     | -> | 1 |
| $G_3$ | 1     | 1     | 0     | 3     | 1     | -> | 2 |
| $G_4$ | 0     | 2     | 0     | 0     | 1     | -> | 3 |
| $G_5$ | 0     | 2     | 0     | 0     | 0     | -> | 4 |

Figure 6:
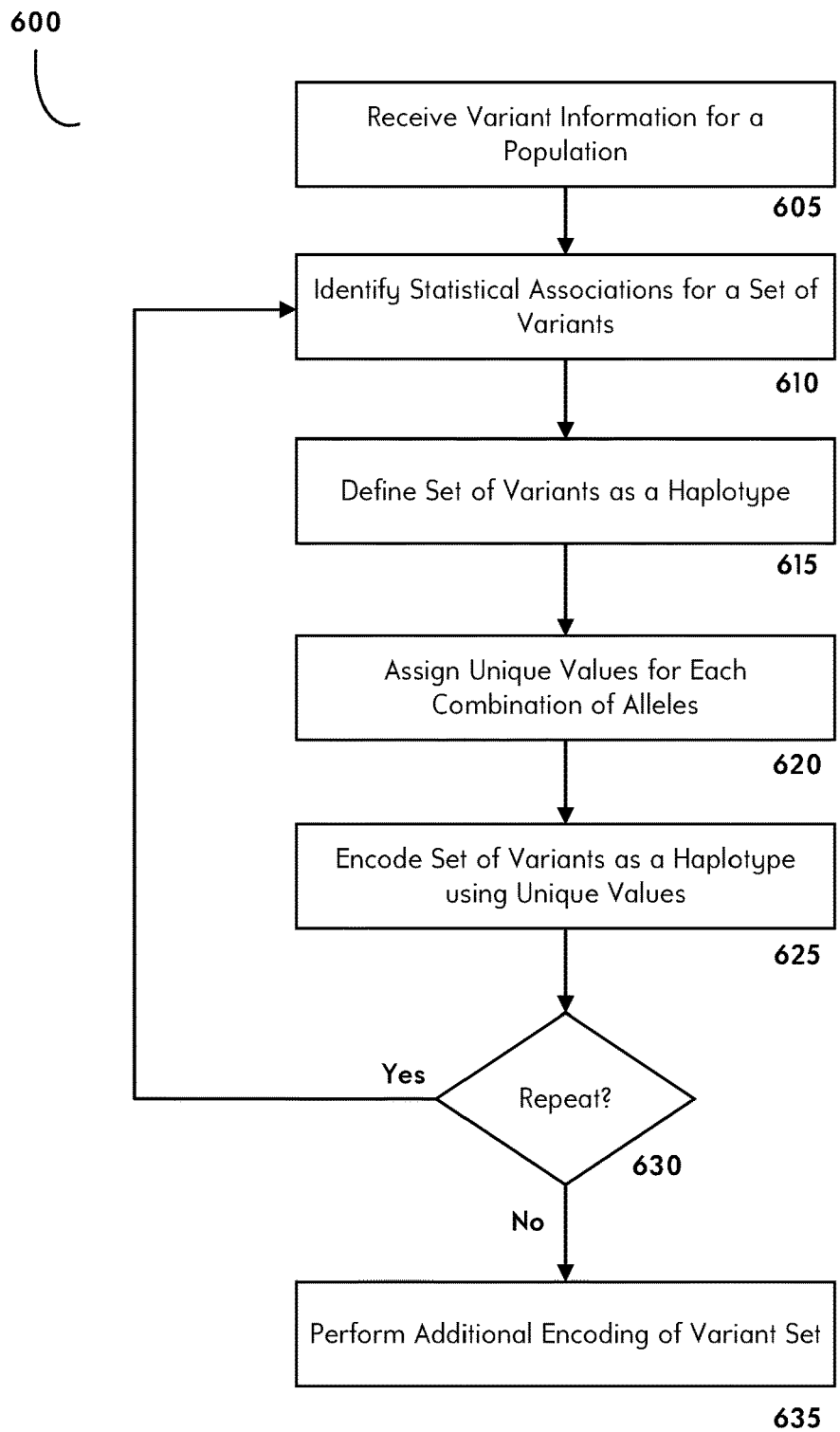

FIG. 6 is a flow diagram depicting an exemplary embodiment of a method 600 of defining haplotypes and encoding variants in a data set based on the defined haplotypes according to the disclosure. The method 600 can be performed in the context of a variant storage system and practiced by a haplotyping agent, such as the variant storage system 100 of FIG. 1 and haplotyping agent 310 of FIG. 3, for example. The method 600 can begin by receiving variant information for a population (step 605). The haplotyping agent 310 may then identify a set of variants which exhibits a relatively low number of actual combinations across the population compared to that expected by chance, i.e., the alleles of the set of variants exhibit statistically significant correlation (step 610). Once a set of variants has been identified, it is defined as a meta-variant, or haplotype (step 615). Each actual combination present in the set of variants is assigned a unique value for the haplotype (step 620). The set of variants may then be encoded using the values for the defined haplotype (step 625).

Identifying haplotypes (step 610) can be performed in a variety of ways. Ideally, a set of variants that leads to a set of haplotypes at or just below powers of 2 increases the efficiency of the representation, as fewer bits are used. However, the improvement fundamentally comes from identifying sets of variants for which the ratio of possible combinations to actual combinations is high. This can be evaluated as follows. The bit cost of storing individual variants ($cost_v$) is:

$$\text{cost}_v = (\Sigma_{i=0}^v \text{bitcount}_{vi}) * p, \quad (1)$$

where p is the number of people in the dataset, and $\text{bitcount}_{vi}$ is the bit count of the ith variant. The cost of storing an aggregated haplotyped variant ($cost_h$) is:

$$\text{cost}_h = \text{bitcount}_h * p + (\Sigma_{i=0}^v \text{bitcount}_{vi}) * \text{valuecount}, \quad (2)$$

where $\text{bitcount}_h$ is the bit count of the aggregated variant haplotype, and valuecount is the number of unique values generated by the haplotype (e.g., the five possible paths represented by the five groups given in the example above). For a haplotyping strategy to be effective, the $cost_h$ must be less than $cost_v$. Effectiveness can also be evaluated by calculating:

$$\text{compression} = \frac{cost_v}{cost_h}, \quad (3)$$

such that positive values represent improvements in bit efficiency.

Figure 7:
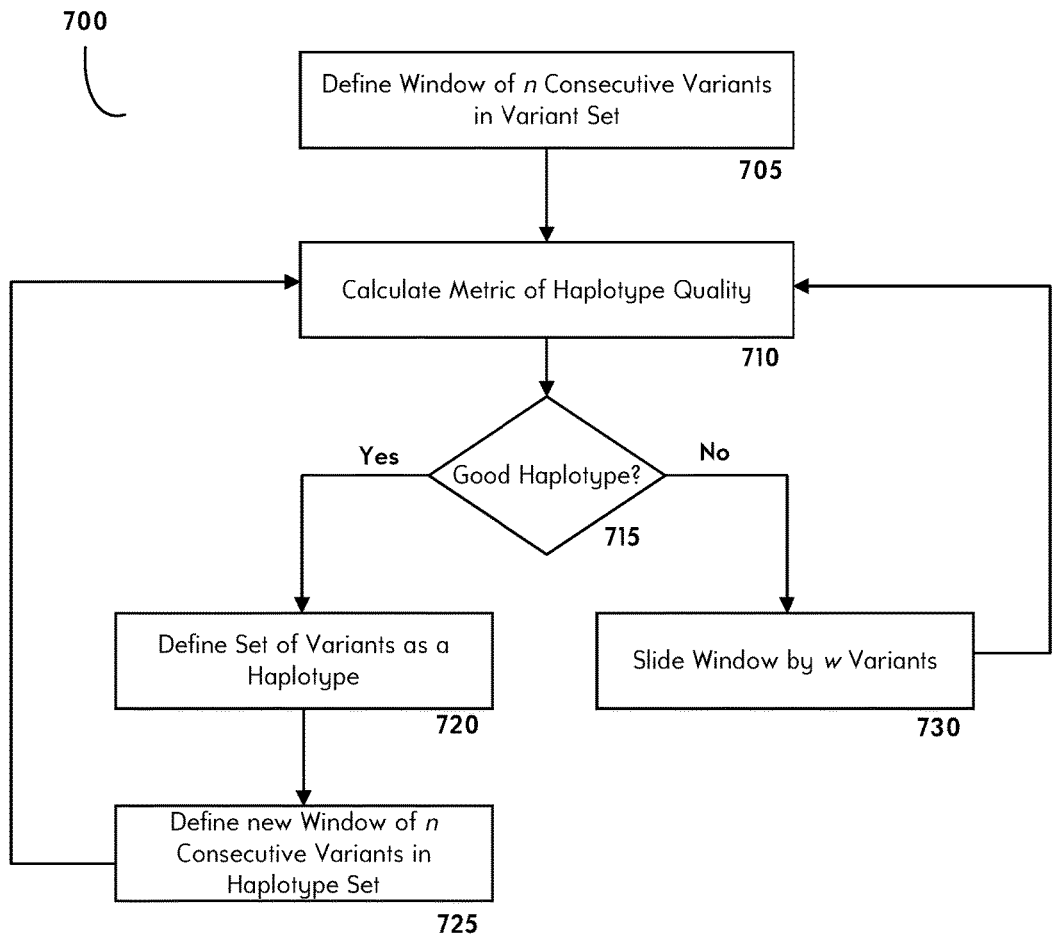

Haplotypes according to the above can be determined in a variety of ways. For example, FIG. 7 depicts an embodiment of a method 700 of identifying haplotypes in a variant set using a sliding window approach, which can similarly be performed by a haplotyping agent 310, for example. The method 700 begins by defining a window of n variants over a variant set (e.g., Table 1 above) (step 705). For the n variants, a metric of haplotype quality is determined (step 710). The metric could be, for example, a measure of whether the actual combinations of the allele values for each variant is low compared to the number of possible combinations. If the present set of variants within the window presents a good haplotype (decision 715), a haplotype is defined for that set (step 720). The set of variants may then be encoded as the defined haplotype, e.g., by using the method 600 of FIG. 6. A new window may then be defined and the method may repeat (step 725). However, if the metric indicates that the present set of variants is not a good haplotype (decision 715), the method 700 may proceed by sliding the window by a certain number of variants (e.g., 1) and repeating the metric (step 730).

While the method 700 describes a sliding window approach for identifying meta-variants or haplotypes within a variant set, other approaches may also be used. For example, instead of using a sliding window, another approach for identifying a haplotype could comprise continuously adding new variants to a set. Whenever the set represents a "good" haplotype (e.g., using a metric as described above), a haplotype is created. In particular, when the addition of a variant affects the metric for haplotype quality, the variant can be rejected for the current haplotype but used to start a new haplotype. Another approach would be to use dynamic programming to calculate an optimal haplotype partitioning for a population or subpopulation. In this case, the haplotyping agent 310 would determine sets of variants that represent the most efficient set of variants for a chosen number of haplotypes or partitions. Such an algorithm would be expected to have a complexity of $O(kn^2)$, where k is the number of partitions, and n is the number of variants. This is sufficiently expensive such that it may be preferable to partition variants into subsets on the order of $10^3$ alleles, and partition each set independently of one another.

Each identified haplotype and its associated variants and genotypes may be stored in an index and later accessed by a variant decoding engine, such as the index 312 and variant decoding engine 124 of FIG. 3, for example. Generating haplotypes can be controlled to increase efficiency. For example, haplotyping can be performed on a variant set prior to encoding using either run length encoding or bit field encoding. However, as low prevalence variants may already be efficiently encoded using run length encoding, in certain embodiments, it can be preferable to simply haplotype only those common variants that would be encoded using bit field encoding. While this may result in reduced coherence (as the variants may be further apart on the chromosome), there are still performance gains compared to strict bit field encoding. As shown in Table 4 below, when applied to the 1000 Genomes Project data set, haplotyping only the bit field encoded variants greatly reduces the amount of storage space required. Here, compression refers to the effectiveness of grouping variants into haplotypes (i.e., as defined in Equation (3) above).

TABLE 4

Storage Improvements from Haplotyping Bit Field Variants

| Bit-field Haplotype Compression | Bit Field Encoded Variants | Run Length Encoded Variants | Total |
|---|---|---|---|
| x1.0 | 4.17 GB | 2.47 GB | 6.64 GB |
| X1.5 | 2.78 GB | 2.47 GB | 5.25 GB |
| X2.0 | 2.10 GB | 2.47 GB | 4.57 GB |
| X2.5 | 1.67 GB | 2.47 GB | 4.14 GB |

Of course, further improvements could be made by applying haplotyping compression to some of the run length encoded variants. For example, as shown in the chart 500 in FIG. 5, there is a point at which run-length encoding is not as efficient, but still performs better than bit-field encoding. These variants could be encoded using haplotyping compression to gain further improvements in efficiency. Further modifications could also be made by segmenting groups within the population. For example, one could exploit coherence within sub-populations, e.g. by separating populations into those of African and European descent, related individuals, etc. (Similarly, an optimal run length entry format could change with population size. One can calculate the optimal run length entry format for each variant at the time that the data is imported.) Various combinations and embodiments of the above methods may be performed in accordance with the disclosure.

Figure 8:
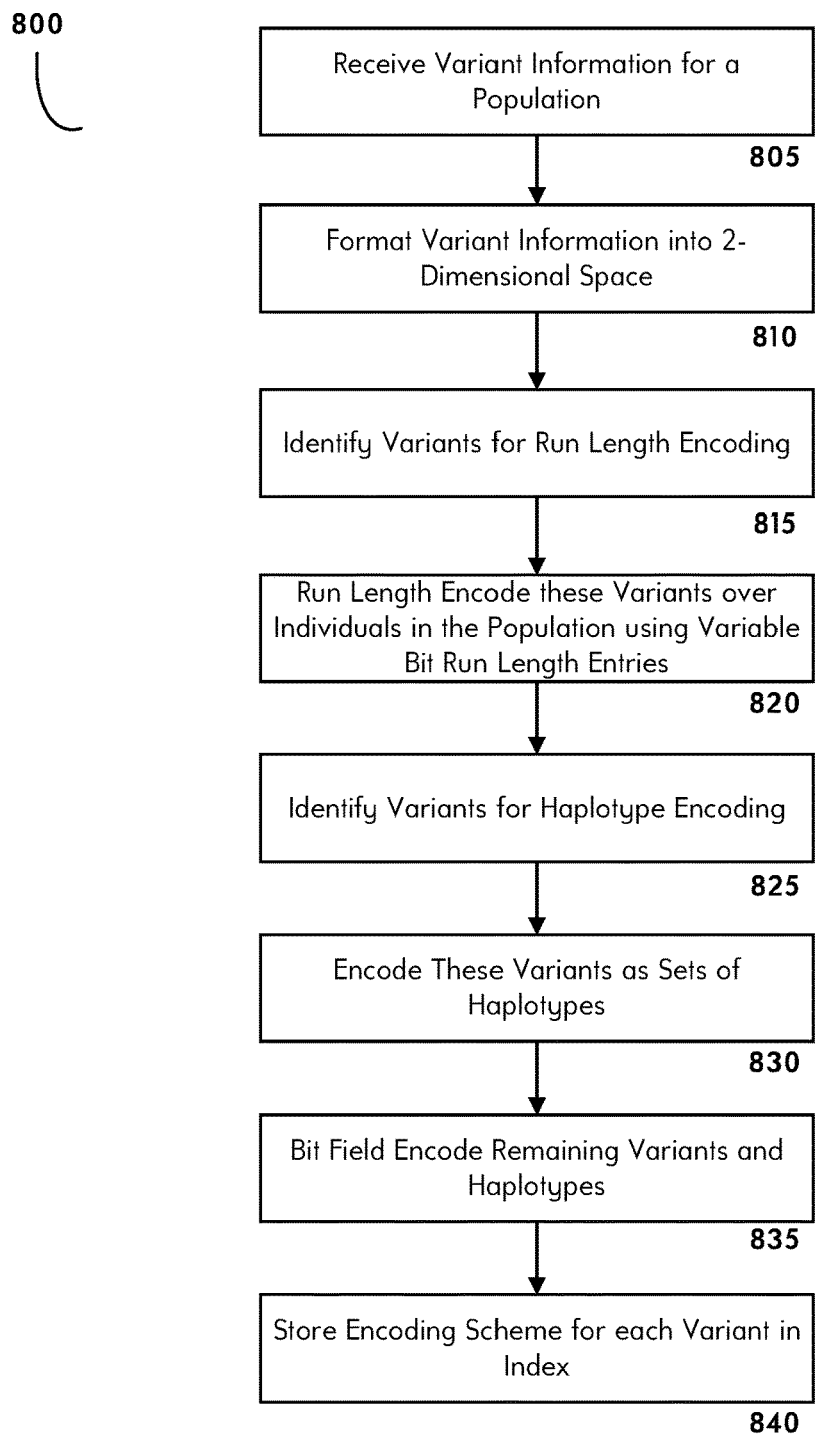

For example, FIG. 8 depicts another embodiment of a method 800 of encoding variation information for a population. The method 800 can similarly be performed by a variant encoding engine in the context of a variant storage system, such as the variant encoding engine 122 and variant storage system 100 of FIG. 1. The method 800 can begin by receiving variant information for a population (step 805). If necessary, the variant information may be formatted into a two-dimensional space, with the individuals in the population in one dimension and the set of variants in a second dimension (step 810). Once properly formatted, the method 800 continues by identifying variants for run length encoding (step 815). This can be performed, for example, by run length encoding those variants having low prevalence within the population (as previously described). To improve efficiency of storage, these variants may be subsequently run length encoded using a variable bit format, in which the run length entries describe the genotypes of a sequence of individuals for each variant (step 820). The remaining variants may then be analyzed to identify statistical associations between variants (step 825) that can be used to encode variants as a reduced set of haplotypes (step 830). The remaining variants (and haplotyped variants) may then be encoded using bit field encoding (step 835). Information regarding how each variant is encoded may be stored in an index, such as the index 312 of FIG. 3; this information may subsequently be used by a variant decoding engine (such as the variant decoding engine 124 of FIG. 1) to appropriately identify and decode the variant for analysis.

Incorporating a haplotyping approach in accordance with the above will likely change the run lengths for non-zero alleles. Accordingly, in certain embodiments, it may be necessary to calculate run length formats based on haplotyped data, which means that run length encoding is performed after haplotyping. Further, when generating haplotypes, it is possible that the increased number of alleles (i.e., possible values for each haplotype) may decrease the efficiency associated with run length encoding rare alleles. Accordingly, in certain embodiments, a hybrid approach may be taken in which meta-variants or haplotypes are only generated from the more common alleles (e.g., based on prevalence, and determined by a prevalence agent, such as the prevalence agent 308 of FIG. 3). In these embodiments, rare alleles are excluded from haplotyping, but can be efficiently encoded using run length encoding.

Additional Bit Savings for Un-Phased Variants

In certain embodiments, systems and methods according to the disclosure can achieve further efficiencies in storage by aggregating ploidy information depending on whether variant data is phased or un-phased. As previously noted, genotypes for individuals may be either phased or un-phased. Phased genotypes are ordered along one chromosome, i.e., there is information describing which particular chromosome on which an allele is present. In contrast, un-phased genotypes simply represent an individual's genotype without regard to which one of the pair of chromosomes holds the allele. In the latter case, further additional benefits can be made with respect to encoding by omitting bits that would be required to represent a phased genotype.

Consider the number of states for phased and un-phased bi-allelic variants:

Two alleles; Phased; 0|0, 0|1, 1|0, 1|1; 4 states; 2 bits
Two alleles; Un-Phased; 0/0, 0/1, 1/1; 3 states; 2 bits This indicates that there is no additional savings to be made for storing single un-phased bi-allelic variants. However, as illustrated in Table 5 below, if the problem is generalized for variants with n alleles, additional bit savings can be achieved for variants having an allele count in excess of two.

TABLE 5

Bits Required for Un-Phased and Phased Variants

| Allele Count | Un-Phased States | Phased States | Bits (Un-Phased) | Bits (Phased) |
|---|---|---|---|---|
| 2 | 3 | 4 | 2 | 2 |
| 3 | 6 | 9 | 3 | 4 |
| 4 | 10 | 16 | 4 | 4 |
| 5 | 15 | 25 | 4 | 5 |
| 6 | 21 | 36 | 5 | 6 |
| 7 | 28 | 49 | 5 | 6 |
| 8 | 36 | 64 | 6 | 7 |
| 20 | 210 | 400 | 7 | 8 |
| n | $\frac{n(n+1)}{2}$ | $n^2$ | $\text{ceil}\left(\log_2\left(\frac{n(n+1)}{2}\right)\right)$ | $\text{ceil}(\log_2 n^2)$ |

Accordingly, encoding un-phased variants may save a few bits for variants having 3 alleles or more. However, this savings is not substantial given that the majority of variations in a population data set are bi-allelic. As shown above, a bi-allelic un-phased variant has only 3 states: 0/0, 0/1, 1/1. The number of states is not a power of two, and so the bits for an individual variant are not fully employed. These additional bits can be used by aggregating un-phased variants.

Consider a set of three un-phased, bi-allelic variants in which homozygous reference (0/0) is represented by 0, heterozygous allele (0/1) is represented by 1, and homozygous allele (1/1) is represented by 2. Thus, the first variant has 3 possible states (0, 1, 2), the second variant has 3 possible states (0, 1, 2), and the third variant has 3 possible states (0, 1, 2). Separately, these three variants require 6 bits (2+2+2) to encode. However, aggregating the possible states across the three variants can reduce the number of bits required. The possible states can be identified by finding all combinations of the three variants, e.g., (V1, V2, V3): (0, 0, 0), (0, 0, 1), (0, 0, 2), (0, 1, 0), (0, 1, 1), and so on (resulting in $3^3$, or 27, possible combinations). 27 possible states requires only 5 bits to encode, resulting in a 1-bit saving compared to storing the variants separately. While this amount may seem negligible, when applied to a population sized data set, the savings can be substantial.

Aggregating un-phased variants provides another way to save bits for phased data (which for phased bi-allelic variants has 4 states, which is a power of 2, and thus there may be no gains via aggregation). The savings can be generalized for aggregating additional variants as follows. Consider a set of n un-phased, bi-allelic variants to be aggregated. The number of potential states S is $S=3^n$ (3 is the number of states for a bi-allelic un-phased variant; as noted above, $$\frac{n(n+1)}{2}$$

is the general case.) The potential savings in bits is given below in Table 6. However, in practice this savings should be balanced against the cost of run length encoding, especially for a set of aggregated variants where one is common and the others are rare.

TABLE 6

Bits Required for Aggregated and Individual Variants

| Variants | Number of States | Bits Required (Aggregated) | Bits Required (Individual) | Savings in Bits |
|---|---|---|---|---|
| 1 | 3 | 2 | 2 | 0 |
| 2 | 9 | 4 | 4 | 0 |
| 3 | 27 | 5 | 6 | 1 |
| 4 | 81 | 7 | 8 | 1 |
| 5 | 243 | 8 | 10 | 2 |
| 6 | 729 | 10 | 12 | 2 |
| 10 | 59049 | 15 | 20 | 5 |
| n | $3^n$ | $\text{ceil}(\log_2 3^n)$ | 2n | $2n - \text{ceil}(\log_2 3^n)$ |

As previously noted, information regarding aggregation of variants and the number of bits used to store each variant may be stored in an index (such as the index 312 of FIG. 3), and consulted when a particular variant is queried and decoded.

III. Conclusion

According to an empirical analysis, the encoding techniques described above result in between 75× and 150× compression over conventional formats, such as uncompressed BCF. Further, because variants are efficiently encoded (as opposed to compressed, which introduces overhead), the encoding techniques allow for interactive querying of large populations totaling tens of thousands of genomes, or larger. Accordingly, the encoding techniques solve the problem of efficiently storing and querying genotype data for large populations, and result in a substantial improvement to the technology of genomic analysis.

Accordingly, a description of various systems and methods for encoding variation information for a population has been provided. Further, it should be noted that various features of the above embodiments and disclosure may be combined with one another to form various variant encoding and extraction systems. The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of encoding variation data for a population, comprising using at least one computer hardware processor connected to at least one non-transitory computer-readable storage medium to perform:
receiving information describing genetic variation of a population of individuals, the information comprising a plurality of variable sites within a reference genome of the population and a plurality of genotypes of a plurality of individuals in the population with respect to those variable sites;
determining a prevalence for each variable site within the population, wherein the prevalence comprises the frequency at which alternative alleles of a given variable site occur in the population;
selecting an encoding strategy for each of the plurality of variable sites based on the determined prevalence of each variable site across the population, wherein if the prevalence for a variable site is less than 10%, less than 5%, less than 1%, or less than 0.1% of the population, the encoding strategy is a compression encoding strategy, and otherwise the encoding strategy is a bit field encoding strategy;
encoding the information according to the encoding strategy selected for each of the plurality of variable sites; and
storing the encoded information in the at least one non-transitory computer-readable storage medium.

2. The method of claim 1, wherein the bit field encoding strategy comprises encoding each genotype as a minimal number of bits.

3. The method of claim 1, wherein the compression encoding strategy is a run length encoding strategy.

4. The method of claim 3, wherein the run length encoding strategy comprises:
for each variable site of the plurality of variable sites:
selecting the genotypes of the plurality of individuals with respect to that variable site, the genotypes comprising a sequence of symbols, the sequence of symbols comprising alternating runs of adjacent identical symbols;
determining, for each run of adjacent identical symbols, a run length; and
encoding the sequence of symbols as a plurality of symbols and run lengths.

5. The method of claim 4, wherein encoding each run length of said runs of adjacent identical symbols uses a variable bit format, wherein the variable bit format comprises a number of bits sufficient to encode the symbol and an associated run length.

6. The method of claim 5, wherein the variable bit format comprises 1 bit to encode a symbol and 3 bits to encode an associated run length.

7. The method of claim 1, wherein encoding the information according to the selected encoding strategy comprises:
identifying a set of variable sites having alleles that occur together with a level of statistical significance;
determining each actual combination of alleles for the identified set of variable sites;
assigning a unique value to each actual combination of alleles; and
encoding the set of variable sites using the assigned unique values.

8. The method of claim 7, wherein identifying a set of variable sites having alleles that occur together with a level of statistical significance comprises identifying a set of variable sites having alleles that exhibit fewer combinations than would be expected by chance.

9. The method of claim 1, wherein encoding the information according to the selected bit field encoding strategy comprises:
identifying a set of variable sites having alleles that occur together with a level of statistical significance;
determining each actual combination of alleles for the identified set of variable sites;
assigning a unique value to each actual combination of alleles; and
encoding the set of variable sites using the assigned unique values and the bit field encoding strategy.

10. A system for encoding variation data for a population, comprising:
a memory, storing information describing genetic variation of a population of individuals, the information comprising a plurality of variable sites within a reference genome of the population and a plurality of genotypes of the plurality of individuals in the population with respect to those variable sites; and
a processor configured to:
for each variable site in the population:
determine the variability of the variable site in the population; and
encode the information associated with the variable site based on the frequency of alternate alleles of the variable site occurring in the population, wherein a variable site having more than 10%, more than 5%, more than 1%, or more than 0.1% frequency of alternate alleles is encoded using a bit field encoding strategy, and otherwise the variable site is encoded using a run length encoding strategy; and
store the encoded information in the memory.

11. A method of encoding variation data for a population, comprising using at least one computer hardware processor connected to at least one non-transitory computer-readable storage medium to perform:
receiving information describing genetic variation of a population of individuals, the information comprising a plurality of variable sites within a reference genome of the population and a plurality of genotypes of a plurality of individuals in the population with respect to those variable sites; and
for each variable site:
calculating a first number of bits required to encode the variable site and its associated genotypes according to a run length encoding strategy, wherein calculating the first number of bits required to encode the variable site according to the run length encoding strategy comprises calculating the number of run length entries required to encode the variable site;

calculating a second number of bits required to encode the variable site and its associated genotypes according to a bit field encoding strategy;

comparing the first number of bits and second number of bits; and encoding, based on the comparison, the variable site and its corresponding genotypes using either the run length encoding strategy or the bit field encoding strategy, wherein the variable site is encoded using the bit field encoding strategy if the first number of bits exceeds the second number of bits, and otherwise the variable site is encoded using the run length encoding strategy.

* * * * *